(12) United States Patent
Freeman et al.

(10) Patent No.: US 9,579,514 B2
(45) Date of Patent: Feb. 28, 2017

(54) IMPEDANCE SPECTROSCOPY FOR DEFIBRILLATOR APPLICATIONS

(71) Applicant: ZOLL Medical Corporation, Chelmsford, MA (US)

(72) Inventors: Gary A. Freeman, Waltham, MA (US); Donald R. Boucher, Andover, MA (US); Frederick J. Geheb, Danvers, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 14/843,843

(22) Filed: Sep. 2, 2015

(65) Prior Publication Data

US 2016/0059023 A1    Mar. 3, 2016

Related U.S. Application Data

(60) Provisional application No. 62/044,809, filed on Sep. 2, 2014.

(51) Int. Cl.
*A61N 1/00*    (2006.01)
*A61N 1/39*    (2006.01)
*A61N 1/365*    (2006.01)

(52) U.S. Cl.
CPC ....... *A61N 1/3925* (2013.01); *A61N 1/36521* (2013.01); *A61N 1/3987* (2013.01)

(58) Field of Classification Search
CPC ... A61N 1/3918; A61N 1/3937; A61B 5/0536
See application file for complete search history.

(56) References Cited

U.S. PATENT DOCUMENTS

| | | | |
|---|---|---|---|
| 5,282,840 A | 2/1994 | Hudrlik | |
| 5,904,706 A * | 5/1999 | Ayati | A61N 1/39 607/5 |
| 5,999,852 A | 12/1999 | Elabbady et al. | |
| 6,473,640 B1 | 10/2002 | Erlebacher | |
| 2003/0125771 A1 | 7/2003 | Garrett | |
| 2005/0107834 A1* | 5/2005 | Freeman | A61N 1/3918 607/5 |
| 2006/0142806 A1 | 6/2006 | Katzman et al. | |
| 2011/0022105 A9 | 1/2011 | Owen et al. | |
| 2012/0143034 A1 | 6/2012 | Gaw | |

(Continued)

OTHER PUBLICATIONS

International Search Report and Written Opinion, PCT/US15/48195, Jan. 8, 2016, 14 pages.

*Primary Examiner* — Robert N Wieland
(74) *Attorney, Agent, or Firm* — Fish & Richardson P.C.

(57) ABSTRACT

A computing device includes a memory configured to store instructions. The computing device also includes a processor to execute the instructions to perform operations that include providing an alternating electrical signal to a patient through at least a pair of electrodes, and determining transthoracic impedance of the patient from a measurement associated with the applied alternating electrical signal. Operations also include identifying, from the transthoracic impedance, a sequence of resistance values for controlling the discharge of a charge storage device located external to the patient, and controlling the discharge of the charge storage device using the identified sequence of resistance values.

37 Claims, 17 Drawing Sheets

(56) References Cited

U.S. PATENT DOCUMENTS

| | | | |
|---|---|---|---|
| 2012/0157797 A1* | 6/2012 | Zhang | A61B 5/002 |
| | | | 600/301 |
| 2012/0221069 A1* | 8/2012 | Rosenberg | A61B 5/686 |
| | | | 607/18 |
| 2013/0023781 A1 | 1/2013 | Freeman et al. | |
| 2013/0338724 A1* | 12/2013 | Joo | A61N 1/3987 |
| | | | 607/3 |

* cited by examiner

| Component | Equivalent Element | Current vs. Voltage | Impedance |
|---|---|---|---|
| Resistor | $R$ [ohm] | $V = IR$ | $R$ |
| Capacitor | $C$ [F, or ohm$^{-1}$ s] | $I = C\, dV/dt$ | $1/j\omega C$ |
| Inductor | $L$ [H, or ohm s] | $V = L\, dI/dt$ | $j\omega L$ |
| Infinite diffusion | $Z_w$ [ohm] | | $R_w / \sqrt{j\omega}$ |
| Finite diffusion | $Z_0$ [ohm] | | $R_D \tanh(\sqrt{(j\omega L_D^2)/D}) / \sqrt{(j\omega L_D^2)/D}$ / $\sqrt{(j\omega L_D^2)/D}$<br>$R_D \coth(\sqrt{(j\omega L_D^2)/D}) / \sqrt{(j\omega L_D^2)/D}$ / $\sqrt{(j\omega L_D^2)/D}$ |
| Constant phase element - CPE | $Q$ [ohm$^{-1}$ s$^\alpha$] | | $\dfrac{1}{Q(j\omega)^a}$ |

FIG. 4

| Target Voltage | Joule Setting | Patient Load 0-23ohms | Patient Load 24-40ohms | Patient Load 41-65ohms | Patient Load 65-115ohms | Patient Load 116-136ohms | Patient Load 161-185ohms | Patient Load 161-205ohms | Patient Load 185-205ohms |
|---|---|---|---|---|---|---|---|---|---|
| | | 0 | 24 | 41 | 65 | 116 | 136 | 161 | 185 |
| 174 | 1 | 60,50,40,30,20,20 | 50,40,30,20,10,00 | 40,30,20,10,00,00 | 40,30,20,10,00,00 | 30,20,10,00,00 | 30,20,10,00,00 | 30,20,10,00,00 | 30,20,10,00,00 |
| 245 | 2 | 60,50,40,30,20,20 | 50,40,30,20,10,00 | 40,30,22,10,00,00 | 40,30,20,10,00,00 | 30,20,10,00,00 | 30,20,10,00,00 | 30,20,10,00,00 | 30,20,10,00,00 |
| 300 | 3 | 60,50,40,30,20,20 | 50,40,30,20,10,00 | 40,30,20,10,00,00 | 40,30,20,10,00,00 | 30,20,10,00,00 | 30,20,10,00,00 | 30,20,10,00,00 | 30,20,10,00,00 |
| 347 | 4 | 60,50,40,30,20,20 | 50,40,30,20,10,00 | 40,30,22,10,00,00 | 40,30,22,10,00,00 | 30,20,10,00,00 | 30,20,10,00,00 | 30,20,10,00,00 | 30,20,10,00,00 |
| 389 | 5 | 60,50,40,30,20,20 | 50,40,30,20,10,00 | 40,30,22,10,00,00 | 40,30,20,10,00,00 | 30,20,10,00,00 | 30,20,10,00,00 | 30,20,10,00,00 | 30,20,10,00,00 |
| 424 | 6 | 60,50,40,30,20,20 | 50,40,30,20,10,00 | 40,30,22,10,00,00 | 40,30,22,10,00,00 | 30,20,10,00,00 | 30,20,10,00,00 | 30,20,10,00,00 | 30,20,10,00,00 |
| 460 | 7 | 60,50,40,30,20,20 | 50,40,30,20,10,00 | 40,30,22,10,00,00 | 40,30,20,10,00,00 | 30,20,10,00,00 | 30,20,10,00,00 | 30,20,10,00,00 | 30,20,10,00,00 |
| 492 | 8 | 60,50,40,30,20,20 | 50,40,30,20,10,00 | 40,30,22,10,00,00 | 40,30,22,10,00,00 | 30,20,10,00,00 | 30,20,10,00,00 | 30,20,10,00,00 | 30,20,10,00,00 |
| 520 | 9 | 60,50,40,30,20,20 | 50,40,30,20,10,00 | 40,30,20,10,00,00 | 40,30,20,10,00,00 | 30,20,10,00,00 | 30,20,10,00,00 | 30,20,10,00,00 | 30,20,10,00,00 |
| 598 | 10 | 60,50,40,30,20,20 | 50,40,30,20,10,00 | 40,30,22,10,00,00 | 40,30,22,10,00,00 | 30,20,10,00,00 | 30,20,10,00,00 | 30,20,10,00,00 | 30,20,10,00,00 |
| 672 | 15 | 60,50,40,30,20,20 | 50,40,30,20,10,00 | 40,30,22,10,00,00 | 40,30,20,10,00,00 | 30,20,10,00,00 | 30,20,10,00,00 | 30,20,10,00,00 | 30,20,10,00,00 |
| 776 | 20 | 60,50,40,30,20,20 | 50,40,30,20,10,00 | 40,30,22,10,00,00 | 40,30,22,10,00,00 | 30,20,10,00,00 | 30,20,10,00,00 | 30,20,10,00,00 | 30,20,10,00,00 |
| 949 | 30 | 60,50,40,30,20,20 | 50,40,30,20,10,00 | 40,30,22,10,00,00 | 40,30,20,10,00,00 | 30,20,10,00,00 | 30,20,10,00,00 | 30,20,10,00,00 | 30,20,10,00,00 |
| 1227 | 50 | 60,50,40,30,20,20 | 50,40,30,20,10,00 | 40,30,22,10,00,00 | 40,30,22,10,00,00 | 30,20,10,00,00 | 30,20,10,00,00 | 30,20,10,00,00 | 30,20,10,00,00 |
| 1449 | 70 | 60,50,40,30,20,20 | 50,40,30,20,10,00 | 40,30,22,10,00,00 | 40,30,20,10,00,00 | 30,20,10,00,00 | 30,20,10,00,00 | 30,20,10,00,00 | 30,20,10,00,00 |
| 1505 | 75 | 60,50,40,30,20,20 | 50,40,30,20,10,00 | 40,30,22,10,00,00 | 40,30,22,10,00,00 | 30,20,10,00,00 | 30,20,10,00,00 | 30,20,10,00,00 | 30,20,10,00,00 |
| 1598 | 85 | 60,50,40,30,20,20 | 50,40,30,20,10,00 | 40,30,22,10,00,00 | 40,30,20,10,00,00 | 30,20,10,00,00 | 30,20,10,00,00 | 30,20,10,00,00 | 30,20,10,00,00 |
| 1737 | 100 | 60,50,40,30,20,20 | 50,40,30,20,10,00 | 40,30,22,10,00,00 | 40,30,22,10,00,00 | 30,20,10,00,00 | 30,20,10,00,00 | 30,20,10,00,00 | 30,20,10,00,00 |
| 1897 | 120 | 60,50,40,30,20,20 | 50,40,30,20,10,00 | 40,30,22,10,00,00 | 40,30,20,10,00,00 | 30,20,10,00,00 | 30,20,10,00,00 | 30,20,10,00,00 | 30,20,10,00,00 |
| 2121 | 150 | 60,50,40,30,20,20 | 50,40,30,20,10,00 | 40,30,22,10,00,00 | 40,30,22,10,00,00 | 30,20,10,00,00 | 30,20,10,00,00 | 30,20,10,00,00 | 30,20,10,00,00 |
| 2222 | 200 | 60,50,40,30,20,20 | 50,40,30,20,10,00 | 30,20,10,00,00 | 30,20,10,00,00 | 10,10,00,00,000 | 10,10,00,00,00 | 00,00,00,00,00 | 00,00,00,00,00 |

FIG. 12

IMPEDANCE SPECTROSCOPY FOR DEFIBRILLATOR APPLICATIONS

PRIORITY CLAIM

This application claims priority to U.S. Provisional Application 62/044,809, filed on Sep. 2, 2014, the entire content of which is incorporated herein by reference.

TECHNICAL FIELD

This document relates to cardiac resuscitation systems and techniques, in particular, defibrillators that apply defibrillation shocks to a patient's heart through electrodes placed externally on the patient's body or externally on the patient's heart during surgery.

BACKGROUND

Heart attacks are a common cause of death. A heart attack occurs when a portion of the heart tissue loses circulation and becomes damaged as a result (e.g., because of blockage in the heart vasculature). Heart attacks and other abnormalities can lead to ventricular fibrillation (VF), which is an abnormal heart rhythm (arrhythmia) that causes the heart to lose pumping capacity. If such a problem is not corrected quickly—typically within minutes—the rest of the body is deprived of oxygen and the person dies. Therefore, prompt care of a person experiencing ventricular fibrillation can be key to a positive outcome for such a person.

One common way to treat ventricular fibrillation is through the use of an electrical defibrillator that delivers a relatively high voltage shock to the heart in order to get it back into a normal pattern and a consistent, strong beat. People who have had previous problems may be implanted with an automatic defibrillator that constantly monitors the condition of their heart and applies a shock when necessary. Other such people may be provided with a wearable defibrillator in the form of a vest such as the LIFEVEST product from ZOLL Medical Corporation. Other people may be treated using an external defibrillator, such as in a hospital or via an automatic external defibrillator (AED) of the kind that is frequently seen in airports, public gymnasiums and other public spaces. Examples of such AEDs are the AED PLUS automated external defibrillator or the AED PRO automated external defibrillator, both from ZOLL Medical Corporation of Chelmsford, Mass.

SUMMARY

The disclosure provides methods and systems that employ impedance spectroscopy techniques to determine complex impedance of patients and use the information in defibrillator operations.

In one aspect, a computing device includes a memory configured to store instructions. The computing device also includes a processor to execute the instructions to perform operations that include providing an alternating electrical signal to a patient through at least a pair of electrodes, and determining transthoracic impedance of the patient from a measurement associated with the applied alternating electrical signal. Operations also include identifying, from the transthoracic impedance, a sequence of resistance values for controlling the discharge of a charge storage device located external to the patient, and controlling the discharge of the charge storage device using the identified sequence of resistance values.

Implementations may include one or more of the following features. Operations of the computing device may include identifying, from the transthoracic impedance, a charge level for the charge storage device, and charging the charge storage device based upon the identified charge level. Determining transthoracic impedance includes executing multiple impedance measurements. At least two of the multiple impedance measurements are used in determining a metric that represents consistency between the measurements. The operations further comprise identifying a predetermined value of impedance for the one or more operations of the defibrillator, upon determining that the metric fails to satisfy a threshold condition. The predetermined value is an impedance value associated with a previous defibrillation performed using the defibrillator. The operations further comprise using the determined transthoracic impedance in one or more operations of a defibrillator. The transthoracic impedance is calculated using at least two frequencies of the alternating electrical signal. A frequency of the alternating electrical signal is approximately 31 KHz. Determining transthoracic impedance of the patient includes measuring voltage across the patient. Determining transthoracic impedance includes executing impedance measurements for multiple frequencies. At least two defibrillation energies or current settings are used by the multiple frequency impedance measurements to estimate an expected impedance. The resistance values of the identified sequence respectively combine with the patient's impedance to maintain a substantially constant impedance level.

In another aspect, a medical device system includes a defibrillator, a memory configured to store instructions, and a processor. The processor executes the instructions to perform operations comprising providing an alternating electrical signal to a patient through at least a pair of electrodes, determining transthoracic impedance of the patient from a measurement associated with the applied alternating electrical signal, wherein both real and complex values are calculated for the transthoracic impedance, and providing an output representing a patient characteristic based on at least one of the real and complex values calculated for the transthoracic impedance.

Implementations may include one or more of the following features. The operations further comprise using the determined transthoracic impedance in adjusting one or more operations of the defibrillator. The transthoracic impedance is calculated using at least two frequencies of the alternating electrical signal. A frequency of the alternating electrical signal is approximately 31 KHz. Determining transthoracic impedance of the patient includes measuring voltage across the patient. Determining transthoracic impedance includes executing impedance measurements for multiple frequencies. At least two defibrillation energies or current settings are used by the multiple frequency impedance measurements to estimate an expected impedance. A lumped circuit model of at least one electrode is estimated based on the measured real and complex impedance values. The lumped circuit model includes estimates of elements of an electrode-electrolyte-skin (EES) interface. The lumped circuit model includes estimates of values of lumped circuit elements of at least one organ of the patient. The at least one organ is the heart. Changes in the estimate of values of lumped circuit elements of the heart are used to detect the flow of blood through the heart. The at least one organ is the lungs. Changes in the estimate of values of lumped circuit elements are used to detect ventilations or spontaneous breathing. The at least one organ is the brain. The value of at least one element of the estimated lumped circuit model is used for artifact reduction in an electrically-based physiologic (EBP) signal. More than two electrodes. Determining transthoracic impedance includes executing multiple impedance measurements. At least two of the multiple impedance measurements are used in determining a metric that represents consistency between the measurements. The operations further comprise identifying a predetermined value of impedance for the one or more operations of the defibrillator, upon determining that the metric fails to satisfy a threshold condition. The predetermined value is an impedance value associated with a previous defibrillation performed using the defibrillator.

In another aspect, a computing device includes a memory configured to store instructions. The computing device also includes a processor to execute the instructions to perform operations that include providing an alternating electrical signal to a patient through at least a pair of electrodes, and determining transthoracic impedance of the patient from a measurement associated with the applied alternating electrical signal. Both real and complex values are calculated for the transthoracic impedance.

Implementations may include one or more of the following features. The real and complex impedance values may be updated at a rate of at least 0.1 Hz. The real and complex impedance values may be measured at two or more frequencies. A lumped circuit model of at least the electrode can be estimated based on the measured real and complex impedance values. The lumped circuit model may include estimates of elements of an electrode-electrolyte-skin (EES) interface. The lumped circuit model may include estimates of values of lumped circuit elements of at least one organ of the patient. At least one organ may be the heart. Changes in the estimate of values of lumped circuit elements of the heart may be used to detect the flow of blood through the heart. At least one organ may be the lungs. Changes in the estimate of values of lumped circuit elements may be used to detect ventilations or spontaneous breathing. At least one organ may be the brain. Changes in the estimate of values of lumped circuit elements may be used to detect flow of blood through the brain. The value of at least one element of the estimated lumped circuit model may be used for artifact reduction in an electrically-based physiologic (EBP) signal. The EBP signal may be an ECG signal. The EBP signal may be an EEG, impedance pneumography or impedance cardiography signal. The computing device may further include more than two electrodes. Changes in the estimate of values of the lumped circuit elements may be used to assess the quality and stability of electrode connection to the patient. For example, an excessive number of significant short term changes in the values of lumped circuit elements may indicate a loose connection between the electrodes and the patient or the presence of other conditions such as chest compressions that may interfere with an accurate assessment of the patient's transthoracic impedance. The additional electrodes may be used to compute an impedance tomograph. The amplitude of the signal is modulated. The frequency of the signal may be modulated.

In another aspect, a method of electrotherapy includes providing an alternating current signal to a patient through a pair of electrodes, and determining transthoracic impedance of the patient from a measurement associated with the applied alternating current signal. The method also includes identifying, from the transthoracic impedance, a sequence of resistance values for controlling the discharge of a charge storage device located external to the patient, and controlling the discharge of the charge storage device using the identified sequence of resistance values.

Implementations may include one or more of the following features. The method may also include identifying, from the transthoracic impedance, a charge level for the charge storage device, and charging the charge storage device based upon the identified charge level. The alternating current signal may have a predefined frequency. The frequency may be approximately 31 KHz. Determining transthoracic impedance of the patient may include measuring current flow through the patient. Determining transthoracic impedance of the patient may include measuring voltage across the patient. Determining transthoracic impedance of the patient may include executing multiple impedance measurements. Determining transthoracic impedance may include executing impedance measurements for multiple frequencies. At least two defibrillation energies or current settings may be used by the multiple frequency impedance measurements to estimate an expected impedance. The measurement for determining the transthoracic impedance may produce a real and imaginary component. The resistance values of the identified sequence respectively may combine with the patient's impedance to maintain a substantially constant impedance level.

In another aspect, a method of electrotherapy includes providing an alternating electrical signal to a patient through at least a pair of electrodes, and determining transthoracic impedance of the patient from a measurement associated with the applied alternating electrical signal. Both real and complex values are calculated for the transthoracic impedance.

Implementations may include one or more of the following features. The real and complex impedance values may be updated at a rate of at least 0.1 Hz. The real and complex impedance values may be measured at two or more frequencies. A lumped circuit model of at least the electrode may be estimated based on the measured real and complex impedance values. The lumped circuit model may include estimates of elements of an electrode-electrolyte-skin (EES) interface. The lumped circuit model may include estimates of values of lumped circuit elements of at least one organ of the patient. At least one organ may be the heart. Changes in the estimate of values of lumped circuit elements of the heart may be used to detect the flow of blood through the heart. At least one organ may be the lungs. Changes in the estimate of values of lumped circuit elements are used to detect ventilations or spontaneous breathing. At least one organ may be the brain. Changes in the estimate of values of lumped circuit elements may be used to detect flow of blood through the brain. As discussed above, electrode connection quality and impedance measurement validity may be detected based upon short term changes in the lumped circuit parameter values. The value of at least one element of the estimated lumped circuit model may be used for artifact reduction in an electrically-based physiologic (EBP) signal. The EBP signal may be an ECG signal. The EBP signal may be an EEG, impedance pneumography or impedance cardiography signal. The method may utilize more than two electrodes. The more than two electrodes may be used to compute an impedance tomography. The amplitude of the signal may be modulated. The frequency of the signal may be modulated.

In another aspect, a computing device includes a memory configured to store instructions. The computing device also includes a processor to execute the instructions to perform operations that include providing one or more alternating electrical signals to a patient through at least a pair of electrodes, and determining transthoracic impedance of the patient from a measurement associated with the applied one or more alternating electrical signals. The transthoracic impedance includes a real and imaginary component. Operations also include using the determined transthoracic impedance in one or more operations of a defibrillator.

Implementations may include one or more of the following features. The transthoracic impedance is used to determine an initial indication of likely effectiveness of a shock applied by the defibrillator. The transthoracic impedance may be used to identify a charge level for a charge storage device of the defibrillator. The transthoracic impedance may be used to identify a sequence of resistance values for controlling a discharge of a charge storage device of the defibrillator. The transthoracic impedance may be processed to provide a ventilation count for the patient. The one or more provided alternating electrical signals may be sinusoidal current signals, each with a different predefined frequency. The measurement may include receiving one or more sinusoidal voltage signals. The one or more provided alternating electrical signals may be sinusoidal voltage signals, each with a different predefined frequency. The measurement may include receiving one or more sinusoidal current signals. Determining transthoracic impedance of the patient may include computing the ratio of one received signal and one of the provided signals, wherein the received signal and provided signal have an equivalent frequency.

In another aspect, a method of electrotherapy includes providing one or more alternating electrical signals to a patient through at least a pair of electrodes, and determining transthoracic impedance of the patient from a measurement associated with the applied one or more alternating electrical signals. The transthoracic impedance may include a real and imaginary component. The method also includes using the determined transthoracic impedance in one or more operations of a defibrillator.

Implementations may include one or more of the following features. The transthoracic impedance may be used to determine an initial indication of likely effectiveness of a shock applied by the defibrillator. The transthoracic impedance may be used to identify a charge level for a charge storage device of the defibrillator. The transthoracic impedance may be used to identify a sequence of resistance values for controlling a discharge of a charge storage device of the defibrillator. The transthoracic impedance may be processed to provide a ventilation count for the patient. The one or more provided alternating electrical signals may be sinusoidal current signals, each with a different predefined frequency. The measurement may include receiving one or more sinusoidal voltage signals. The one or more provided alternating electrical signals may be sinusoidal voltage signals, each with a different predefined frequency. The measurement may include receiving one or more sinusoidal current signals. Determining transthoracic impedance of the patient may include computing the ratio of one received signal and one of the provided signals, wherein the received signal and provided signal have an equivalent frequency.

In another aspect, a computing device includes a memory configured to store instructions. The computing device also includes a processor to execute the instructions to perform operations that include providing an alternating electrical signal to a patient through at least a pair of electrodes, and determining transthoracic impedance of the patient from a measurement associated with the applied alternating electrical signal. The transthoracic impedance is calculated using at least two frequencies of the alternating electrical signal.

Implementations may include one or more of the following features. The transthoracic impedance determination may be updated at a rate of at least 0.1 Hz. The transthoracic impedance may be measured at two or more frequencies. A lumped circuit model of at least the electrode may be estimated based on the measured transthoracic impedance. The lumped circuit model may include estimates of elements of an electrode-electrolyte-skin (EES) interface. The lumped circuit model may include estimates of values of lumped circuit elements of at least one organ of the patient. At least one organ may be the heart. Changes in the estimate of values of lumped circuit elements of the heart may be used to detect the flow of blood through the heart. At least one organ may be the lungs. Changes in the estimate of values of lumped circuit elements may be used to detect ventilations or spontaneous breathing. At least one organ may be the brain. Changes in the estimate of values of lumped circuit elements may be used to detect flow of blood through the brain. Changes in the values of lumped circuit parameters may also be used to assess electrode connection and quality. The value of at least one element of the estimated lumped circuit model may be used for artifact reduction in an electrically-based physiologic (EBP) signal. The EBP signal may be an ECG signal. The EBP signal may be an EEG, impedance pneumography or impedance cardiography signal. The computing device may include more than two electrodes. More than two electrodes may be used to compute an impedance tomography. The amplitude of the signal may be modulated. The frequency of the signal may be modulated.

In another aspect, a method of electrotherapy includes providing an alternating electrical signal to a patient through at least a pair of electrodes, and determining transthoracic impedance of the patient from a measurement associated with the applied alternating electrical signal. The transthoracic impedance is calculated using at least two frequencies of the alternating electrical signal.

Implementations may include one or more of the following features. The transthoracic impedance may be updated at a rate of at least 0.1 Hz. The transthoracic impedance may be measured at two or more frequencies. A lumped circuit model of at least the electrode may be estimated based on the measured real and complex impedance values. The lumped circuit model may include estimates of elements of an electrode-electrolyte-skin (EES) interface. The lumped circuit model may include estimates of values of lumped circuit elements of at least one organ of the patient. At least one organ may be the heart. Changes in the estimate of values of lumped circuit elements of the heart may be used to detect the flow of blood through the heart. At least one organ may be the lungs. Changes in the estimate of values of lumped circuit elements may be used to detect ventilations or spontaneous breathing. At least one organ may be the brain. Changes in the estimate of values of lumped circuit elements may be used to detect flow of blood through the brain. The value of at least one element of the estimated lumped circuit model may be used for artifact reduction in an electrically-based physiologic (EBP) signal. The EBP signal may be an ECG signal. The EBP signal may be an EEG, impedance pneumography or impedance cardiography signal. More than two electrodes may be utilized. The more than two electrodes may be used to compute an impedance tomography. The amplitude of the signal may be modulated. The frequency of the signal may be modulated.

Other features and advantages will be apparent from the description and drawings, and from the claims.

DESCRIPTION OF DRAWINGS

FIG. 4 is a chart that represents ideal circuit elements for equivalent circuit models for impedance spectroscopy.

FIG. 12 presents a table of resistance schedules for producing electrotherapy waveforms.

Like reference symbols in the various drawings indicate like elements.

DETAILED DESCRIPTION

The present disclosure is directed to systems and methods for using impedance spectroscopy for defibrillator operations such as determining transthoracic impedance (TTI). In general, defibrillation is a common treatment for various arrhythmias, such as ventricular fibrillation (VF). Transthoracic impedance of a patient may be used for various defibrillator operations associated with treatment. For example, along with using the impedance to set defibrillator operational parameters (e.g., capacitor charge level, selecting parameters to maintain output current, etc.), the impedance can be used for patient monitoring (e.g., count ventilations applied to the patient). By measuring the impedance as a complex quantity, as provided by impedance spectroscopy, additional information may be obtained from the impedance of the patient's body to assist with treatment.

Figure 1:
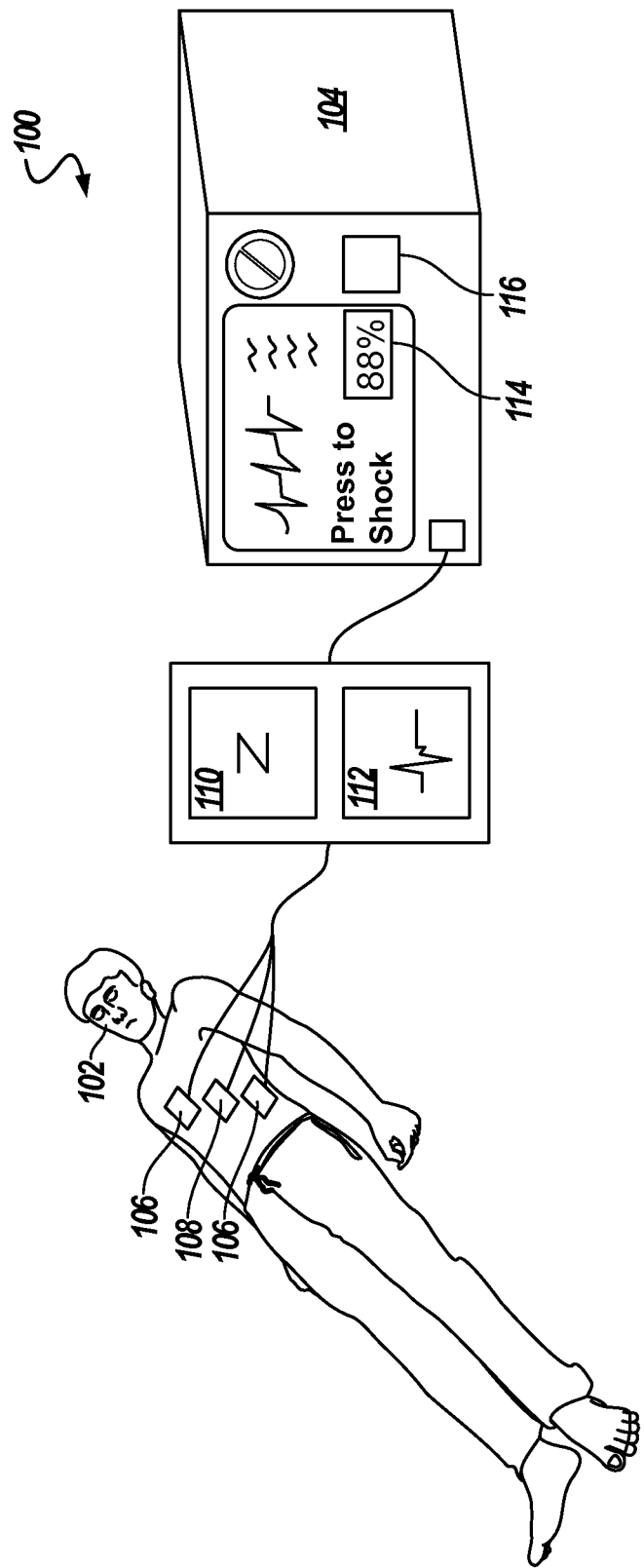
FIG. 1 shows a victim of cardiac arrest being cared for by a rescuer.

FIG. 1 shows a victim 102 of cardiac arrest being cared for by a rescuer (not shown) and a defibrillator 104. The defibrillator 104 includes an electrode package 106 and can optionally include a compression puck 108 generally coupled thereto. Other embodiments of the defibrillator 104 are possible.

In the pictured example, the victim 102 is rendered prone due to an arrhythmic episode, and the electrode package 106 and the compression puck 108 are positioned on the torso of the victim 102 in an appropriate and known arrangement. In accordance with the present disclosure, the defibrillator 104, in tandem with one or both of the electrode package 106 and the compression puck 108, is configured to provide signals and information to determine the impedance of the patient (e.g., TTI) and then use this information to assist with treatment.

For example, the defibrillator 104 is configured to acquire and manipulate both a TTI signal 110 and an electrocardiogram (ECG) signal 112 via the electrode package 106. As described in further detail below, a TTI measurement ($\Omega$) is a parameter derived from the TTI signal 110 that represents, among other things, thoracic fluid content. An amplitude spectrum area (AMSA) value (V-Hz) is a parameter calculated by integrating the Fourier transform of the ECG signal 112 over a finite frequency range. The AMSA value is one form of calculation that represents a value of an ECG signal from a victim, while other values may likewise be computed.

The defibrillator 104 is further configured to display an indicator 114 based on the TTI measurement(s), AMSA value(s), etc. obtained from the TTI signal 110 and an ECG signal 112, respectively. For example, the indicator 114 may provide a perceptible cue that suggests whether or not a particular defibrillation event will likely terminate the arrhythmic episode of the victim 102. As illustratively presented, when the indicator 114 displays a success indication of "88%," the rescuer can be instructed "Press to Shock" to apply a shock to the victim 102 via actuation of a control 116. Other embodiments are possible. For example, it will be appreciated that a success indication or other type of information may be provided as any type of perceptible feedback (e.g., haptic, audio, etc.). In certain implementations, the defibrillator 104 may make a determination using the TTI (e.g., select charge level) without expressly notifying the rescuer. In other situations, the defibrillator 104 may explicitly indicate the determination (e.g., likelihood of shock success), e.g., by showing a percentage likelihood as indicated in FIG. 1, by showing less discrete gradations for success (e.g., poor, good, very good, and excellent), or by displaying a range of colors (e.g., with red indicating a poor chance and green indicating a good chance).

The impedance provided by the TTI signal 110 may be used for a variety of operations of the defibrillator 104, for example, based upon the measured impedance, the defibrillator 104 may adjust the amount of voltage applied to the victim's heart during defibrillation in order to deliver a uniform current flow to patients of different impedances. The impedance across the patient's chest can also be used to detect the airflow activities (e.g., respiration, ventilation, etc.) of the victim. As the patient's lungs expand and contract, the geometry of the patient's chest changes that causes the measured impedance to correspondingly change.

Often in such situations the patient is ventilated by sealing a ventilation bag (not shown) around the mouth of the patient 102. The ventilation bag may, for the most part, take a familiar form, and may include a flexible body structure that the rescuer may squeeze periodically to provide ventilation on the patient 102 when the patient is not breathing sufficiently on his or her own. Over ventilating the patient 102 (e.g., due to an overly-excited novice rescuer), may cause a variety of repercussions. For example, inflating the victim's lungs too frequently may result in excess pressure being placed on the victim's heart that can restrict the supply of blood being provided to the heart and circulated throughout the patient's body. As such, monitoring the ventilations being applied to the victim through the TTI signal 110 and providing the rescuer feedback regarding the ventilations (e.g., inform the rescuer to reduce the frequency of ventilations, etc.) may be crucial for the patient's blood circulation.

Figure 2:
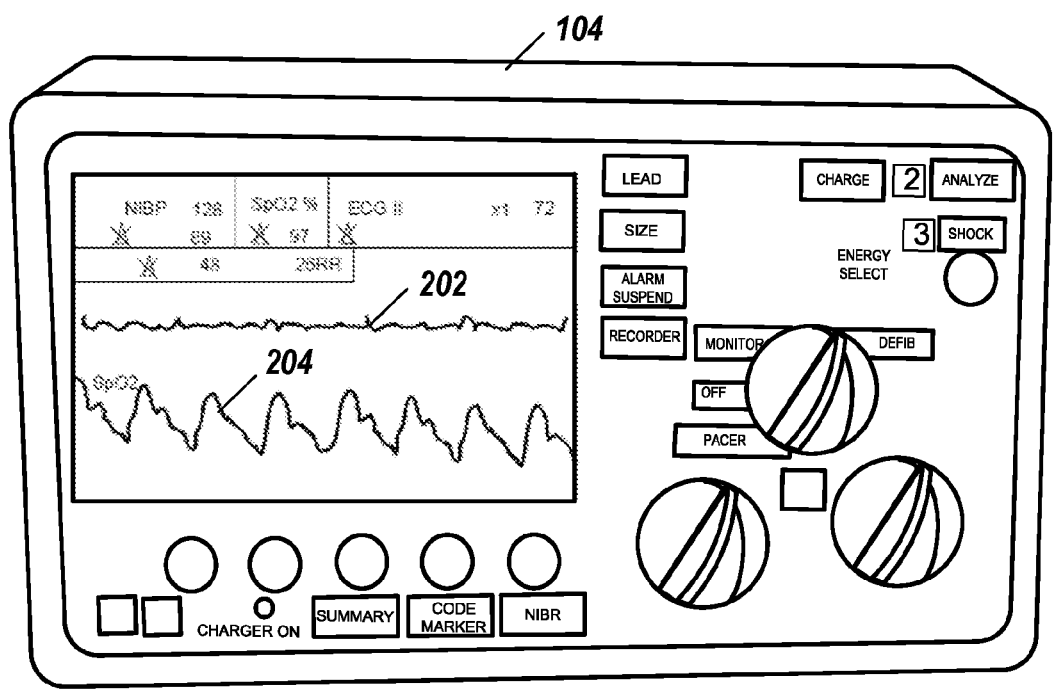
FIG. 2 illustrates a defibrillator showing certain types of information that can be displayed to a rescuer.

Referring to FIG. 2, a defibrillator shows certain types of information that can be displayed to a rescuer. In the figure, the defibrillator 104 with a display portion 200 provides information about patient status and CPR administration quality during the use of the defibrillator device. As shown on display 200, the defibrillator 104 displays a filtered ECG waveform 202 and a SpO2 waveform 204 (alternatively, a CO2 waveform can be displayed).

During chest compressions, the ECG waveform is generated by gathering ECG data points and accelerometer readings, and filtering the motion-induced (e.g., CPR-induced) noise out of the ECG waveform. In general, displaying the filtered ECG waveform helps a rescuer reduce interruptions in CPR because the displayed waveform is easier for the rescuer to decipher. If the ECG waveform is not filtered, artifacts from manual chest compressions can make it difficult to discern the presence of an organized heart rhythm unless compressions are halted. Filtering out these artifacts can allow rescuers to view the underlying rhythm without stopping chest compressions. In some arrangements, information from the collected TTI signal 110 may be used to process these other signals. Such a reminder can be coordinated with other feedback as well, and can be presented in an appropriate manner to get the rescuer's attention. The visual indication may be accompanied by additional visual feedback near the rescuer's hands, and by a spoken or tonal audible feedback, including a sound that differs sufficiently from other audible feedback so that the rescuer will understand that release (or more specifically, lack of release) is the target of the feedback.

Figure 3:
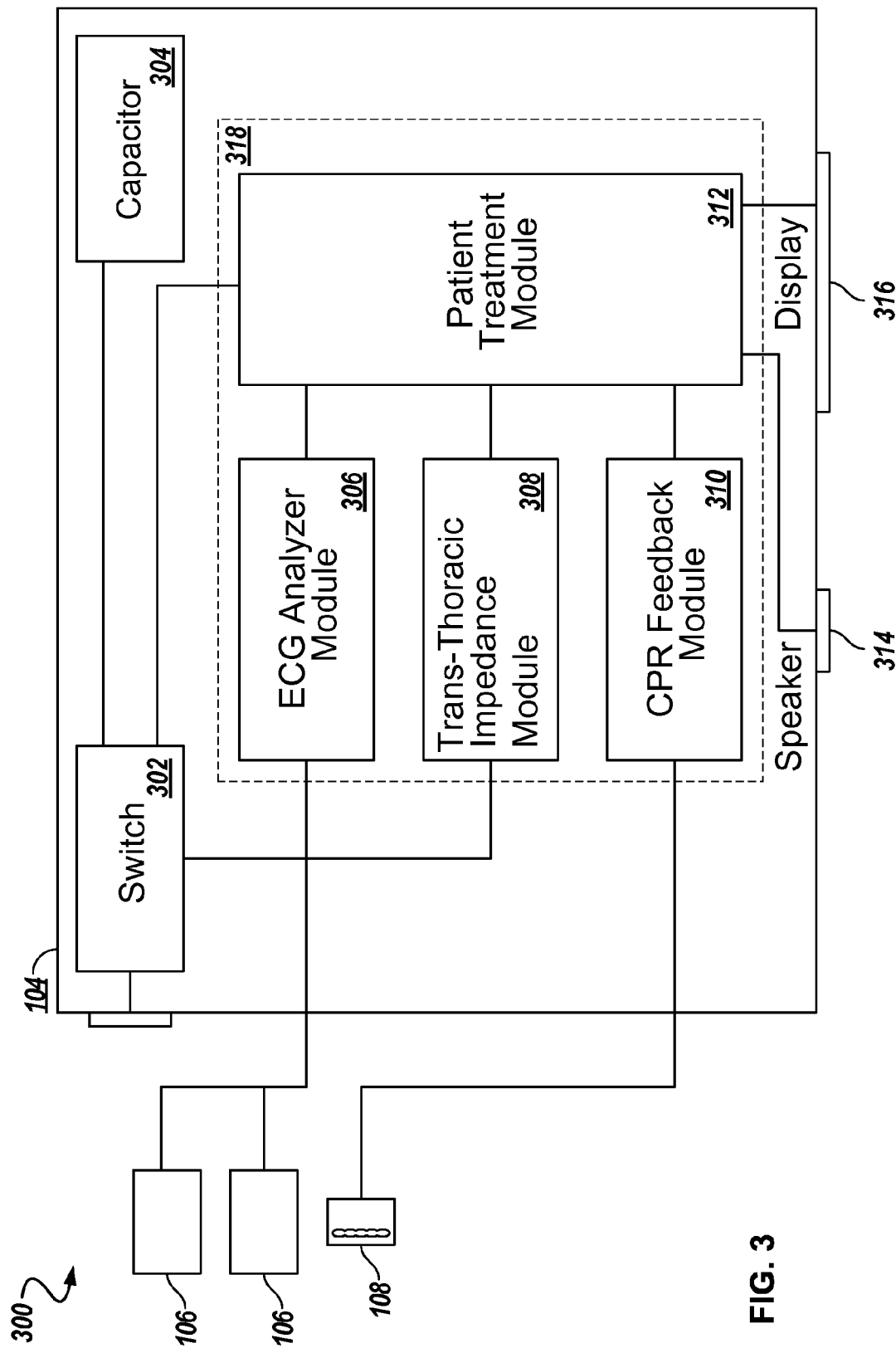
FIG. 3 is a block diagram that shows a defibrillator with an electrode package and compression puck.

Referring now to FIG. 3, a schematic block diagram 300 shows the example defibrillator 104, along with the example electrode package 106 and compression puck 108, of FIG. 1 in more detail. In general, the defibrillator 104, and optionally one or more of the electrode package 106 and compression puck 108, defines an apparatus for administering care to a patient, subject, or individual (e.g., victim 102) who requires cardiac assistance.

The defibrillator 104 includes a switch 302 and at least one capacitor 304 for selectively supplying or applying a shock to a subject. The defibrillator 304 further includes an ECG analyzer module 306, a TTI module 308, a CPR feedback module 310 for controlling the frequency and magnitude of chest compressions applied to a subject, a patient treatment (PT) module 312, a speaker 314, and a display 316. In this example, the ECG analyzer module 306, TTI module 308, CPR feedback module 310, and patient treatment (PT) module 312 are grouped together as a logical module 318, which may be implemented by one or more computer processors. For example, respective elements of the logical module 318 can be implemented as: (i) a sequence of computer implemented instructions executing on at least one computer processor of the defibrillator 104; and (ii) interconnected logic or hardware modules within the defibrillator 104, as described in further detail below in connection with FIG. 17.

In the example of FIG. 2, the electrode package 106 is connected to the switch 302 via port on the defibrillator 104 so that different packages may be connected at different times. The electrode package may also be connected through the port to ECG analyzer module 306, and TTI module 308.

The compression puck 108 is connected, in this example, to the CPR feedback module 310. In one embodiment, the ECG analyzer module 306 is a component that receives an ECG (e.g., ECG signal 112 shown in FIG. 1). Similarly, the TTI module 308 is a component that receives transthoracic impedance (e.g., TTI signal 110 also shown in FIG. 1). Other embodiments are possible. For example, the functionality of the modules 306, 308, and 310 may be combined or distributed in different manners. Further the signals received by the modules (e.g., ECG signal 112 and TTI signal 110) may be differently distributed.

The PT module 312 is configured to receive an input from each one of the ECG analyzer module 306, TTI module 308, and CPR feedback module 310. The PT module 312 uses inputs as received from at least the ECG analyzer module 306 and TTI module 308 for various functions, e.g., predicting whether a defibrillation event will likely terminate an arrhythmic episode, detect when the patient is being over ventilated, etc. Information from these modules such as TTI module 308 may be used for setting one or more operational parameters of the defibrillator 104 (e.g., set capacitor charge level, selecting parameters to maintain current flow, etc.). The impedance signal (provided to the TTI module 308) measured across the chest of the patient 102 may be processed to represent airflow activities (e.g., ventilations, unassisted breathing by the patient, etc.) and to determine, for example, if the patient 102 is being properly ventilated. In this manner, the PT module 312 can use information derived from both ECG, transthoracic impedance, chest compressions, etc. to provide treatment assistance.

The PT module 316 is further configured to provide an input to each one of the speaker 314, display 316, and switch 302. In general, input provided to the speaker 314 and a display 316 relates to treatment of the patient 102 (e.g., indicating success or failure of delivered shocks, indicating the likelihood of a success shock being delivered, providing airflow activity feedback for potential adjusting of assisted/artificial ventilation activities, providing feedback related to CPR treatment of the patient, etc.).

For measuring transthoracic impedance, tissue of the patient 102 can be considered an aggregate of cells surrounded by fluids. Each cell is surrounded by a membrane that envelops intracellular fluids, and the cells are mainly composed of lipids and proteins and smaller amounts of other substances such as water and sugar. One theory is that, by imposing currents with low sinusoidal frequencies for the TTI measurements, cellular membrane can be considered as having relatively high resistance and therefore, the current travels through the extracellular fluids around the cells. According to this theory, for higher frequency current signals, the capacitance of the cellular membrane can short circuit the resistance of the membrane; and the current passes more uniformly through the tissue. As such, tissue impedance generally decreases with frequency due to the short circuiting of the cellular membrane resistance. According to this frequency dependent impedance theory, the membrane of a cell can be electrically modeled with complex components, e.g., having a capacitive component and a resistive component (e.g., representable as a capacitor in parallel with a resistor). The extracellular fluids can also be modeled as having a resistive component, which can be combined with the electrical model of the cell membrane (e.g., by connecting another resistor in parallel or series with the capacitor/resistor model of the cell membrane). Due to the capacitive and resistive elements of the electrical model, tissue impedance can be considered as a complex quantity, e.g., complex series impedance (resistance in series with reactance) or complex parallel admittance (conductance in parallel with capacitance). While impedance is primarily referred to in this disclosure, the described techniques could be adjusted to utilize admittance.

One or more quantities may be measured to determine tissue impedance such as TTI, for example, the degree to which a material conducts electricity (conductivity ($\sigma$) or its reciprocal resistivity ($\Omega$)) may be measured along with the ability of the tissue to store electrical energy (permittivity ($\in$)).

The understanding under the presently discussed theory is that tissue impedance generally decreases slowly with an increase in frequency, due to the cellular structure of tissues and the frequency dependence of the membrane characteristics. This is described in further detail below with respect to FIGS. 16A-16C. This frequency dependency can vary based upon variations of permittivity with frequency caused by interfacial polarizations and surface ionic conduction at membrane boundaries, membrane capacitance shorting the membrane resistance, the relaxation of water molecules in the intracellular fluid, etc. When applying a sinusoidal voltage signal to the complex-impedance tissue for a TTI measurement, two current types flow: a conduction current that is independent of frequency and a displacement current that is frequency dependent. By sensing this induced current from the applied voltage signal, the TTI module 308 may determine the TTI.

Similar to the understanding that tissue impedance changes with frequency, it is understood that impedance may vary based on other factors such as tissue temperature (e.g., tissue impedance generally decreases with increasing temperature) and structural changes. For example, lung volume changes during inhalation and expiration, and can cause impedance changes (e.g., larger impedance values are typically measured during inhalation compared to expiration). The presence of or flow of blood through the tissue can also effect impedance such as TTI. Other portions of a patient's body may effect complex impedance measurements due to their frequency dependent impedances. For example, skin generally includes stratum corneum, which is composed of layers of dead cells, and can produce relatively high impedance levels for high frequency signals. Typically the outermost layers account for the impedance of the skin and impedance levels significantly drop for the inner skin layers. Similar to tissue, skin impedance can be treated as a complex quantity and modeled in similar manner as membrane resistance and capacitance, along with resistance for intracellular and extracellular fluids.

Similar to portions of the patient (e.g., tissue, skin, etc.) and patient movement (e.g., lung volume changes due to inhaling and exhaling), other mechanisms may contribute to complex components of measured transthoracic impedance. Equipment used in TTI measurements may contribute to these components. For example, each electrode attached to a patient's torso is generally considered a transducer that converts electrical current (provided by a conductor from the defibrillator 104) to an ionic current in the electrolyte tissue of the patient. In general, the impedance of the electrode/skin interface should be relatively small and can be accounted for so as to not corrupt the impedance measurements. To reduce potential effects, the electrodes may be coated to improve the contact between the conductive material of the electrodes and the patient (e.g., electrodes can be coated in salt, a viscous saline gel, etc.). Various material types may be employed for improved contact; for example, non-corrosive materials such as stainless steel, conductive rubber, etc. In general, contact impedance at the electrode/skin interface decreases as frequency increases (for applying sinusoidal signals), and in general is relatively small compared to the patient's skin contribution to the complex impedance. Electrode size and geometry can also effect impedance measurements since conductance generally increases with conductive area. Further, the number of electrodes employed can affect impedance measurements, for example, rather than using a two-electrode system as illustrated in the figure (where one electrode provides current to the other electrode), four or more electrodes may be used with a defibrillator in which current is introduced on multiple electrodes and voltage is measured across more than one electrode pair.

Independent of the number of electrode pairs, various types of measurements may be employed to determine the complex impedance (e.g., TTI) of the patient; for example, a known current signal (e.g., a sinusoidal signal, constant level signal, modulated signal, etc.) is injected and a corresponding voltage signal is measured across the electrode pair, or, a voltage signal is applied across the electrodes and the current flow between the electrodes is measured. Using the same electrodes to both deliver and sense signals, one or more switching devices, switching networks, etc. or other types of circuitry can be employed to switch between applying the current, voltage, etc. signal and then sensing the resulting voltage, current, etc. signal for computing the impedance between the electrodes. For example, TTI module 308 may use various combinations of circuitry, microprocessor based systems, etc. to apply the signals, receive response signals and compute the complex impedance. For systems in which a current signal is injected (from one electrode to another), the measured voltage can span over a considerable range (e.g., from less than a millivolt to over tens of volts). Once collected and processed (e.g., filtered, amplified, demodulated, etc.) the analog signal may be sampled for producing discrete signals (e.g., quantized signal levels) to determine corresponding impedance levels. Implementations for producing, collecting and processing such signals are described in "Electrical Impedance Tomography," Webster, J. G., Adam Hilger, 1990, which is incorporated by reference herein in its entirety.

Various types of signals may be applied to the electrode package 106 to perform the impedance measurements. For example, signals having different characteristics (e.g., phase, frequency, etc.) may be introduced to the patient's body. By applying signals (e.g., sinusoidal current or voltage signals) that each have a different frequency (e.g., from a predefined frequency list), or a range of frequencies (e.g., via a chirp signal, incrementally increasing or decreasing frequencies over a time period), etc., the resulting complex components can be quantified. In addition to using sinusoidal signals as input signals, some impedance spectroscopy techniques may insert substantially constant level (DC) current or voltage signals and measure corresponding voltages or currents across the electrodes of the electrode package 106.

Upon collecting the response signals, the impedance may then be calculated as a function for frequency from the signals (e.g., calculating the complex impedance from the ratio of the input current or voltage signal and the measured voltage or current signal). TTI module 308 would typically employ a microprocessor based system for executing the operations, however, other types of circuitry and/or processing techniques may be utilized. By employing these measurement techniques, both resistive and capacitive components of the response signal, containing the excitation frequency and its harmonics are determined by the TTI module 308 for each frequency.

Along with employing one or more microprocessors to perform these measurements, TTI module 308 may use other types of circuitry. For example, bridge circuits (e.g., a Wien Bridge, Wheatstone bridge, Maxwell bridge, etc.) may be employed that can determine impedance values by comparing measured values to known impedance values. By connecting an unknown impedance to one arm of a bridge, the other arms of the bridge can be adjusted (e.g., nulling the bridge) to reveal the unknown impedance. Using a Wien bridge, capacitance values may be measured in terms of resistance and frequency. Bridge variations may also be implemented dependent upon the frequency range of the signals used in the TTI measurements, for example, transformer ratio arm bridges, Berberian-Cole Bridges, and auto-balance bridges may be used to determine unknown impedance for particular ranges.

Once the complex impedance data is determined, TTI module 308 (alone or in combination with PT module 312) can process the data to identify information for assisting with operations of the defibrillator 104, patient treatment, etc. For example, by performing one or more processes (e.g., calculating an estimated value, filtering, weighting, etc.) a single complex value may be determined to represent the impedance of the patient's body. The processing may account for other quantities such as electrode impedance, temperature, calibration data, etc. to attain an impedance level for quantifying the charge exchanging capability of a patient's body.

Similar to determining the complex impedance over frequency, representative models may be developed for applications (e.g., provided by TTI module 308, PT module 312, etc.) from the collected data. For example, measured data can be fit to an equivalent electrical circuit model (e.g., ideal resistors and capacitors used to represent the impedance over frequency) by comparing the idea models against the measured data. Typically the models employ common electrical elements such as resistors, capacitors, and inductors. The impedance of a resistor is independent of frequency and only has a real impedance component. Absent the imaginary component of the impedance, the current through the resistor is considered to be in phase with the voltage measured across it. Since the impedance of an inductor increases with frequency, inductors have an imaginary impedance component and an inductor's current is phase-shifted by +90° with respect to the voltage. The impedance versus frequency of a capacitor can be considered opposite to that of an inductor. A capacitor's impedance decreases as frequency is raised, as such capacitors also have an imaginary impedance component and the current through the capacitor is phase-shifted −90° with respect to the voltage. Referring to FIG. 4, a chart 400 provides a listing of the common circuit elements used for equivalent circuit models, the equations for their current-voltage relationship and their impedance as provided from "Impedance Spectroscopy, Applications to Electrochemical and Dielectric Phenomena" by Vadim Lvovich, A John Wiley & Sons, Inc. Publication, July 2012, which is herein incorporated by reference in its entirety.

Equivalent electrical circuit models can be considered as attempting to represent complex impedance with electrical components, however, for some arrangements, distributed circuit elements may be needed in addition to the ideal circuit elements to describe the measured impedance. As provided in the chart 400, these distributed circuit elements can include a constant phase element, infinite diffusion and finite diffusion (also collectively known as Warburg diffusion impedance).

By using such impedance spectroscopy techniques to determine the impedance over frequency along with other quantities (e.g., estimated value of impedance, variance, equivalent circuit models, etc.), the TTI module 308, the PT module 312 and other portion of the defibrillator 104 can employ this information for various operations. For example, the determined impedance can be used to select various voltage levels for charging the capacitor 304 of the defibrillator 104. A table may be prepared (as described with respect to FIG. 12) that presents a series of voltage level selections based upon the measured impedance and the energy level selected for defibrillation (e.g., 50 Joules (J), 70 J, 85 J, 150 J and 200 J). Along with the selectable energy level, the table may also identify ranges of impedance to select the needed voltage level. For example, for a selected energy level of 50 J, the voltage level is determined based upon the patient impedance falling within a range (e.g., from 10Ω to 22Ω, 22Ω to 65Ω, or greater than 65Ω). Based upon the energy level selected and the patient impedance, the table provides one or more voltage levels (e.g., a target voltage level, a safety-based maximum voltage, and a refresh voltage. Alternatively, for some embodiments, the measured impedance and selected energy dosage may be used to compute a target voltage for capacitor charging, for example, based on a suitably developed relationship. Such a relationship may employ the real part of the measured impedance, the imaginary part of the measured impedance and/or simply the magnitude of the measured impedance computed as the square root of the real part squared plus the imaginary part squared.

In this example, the real component of the complex impedance is used for selecting the voltage levels, however; other quantities may be used (e.g., impedance magnitude, etc.) as determined from the complex impedance. Similar to selecting the voltage levels other quantities for defibrillator operations may be selected using the impedance such as parameters associated with the discharge waveform (e.g., resistance levels, resistor schedules, etc.).

Measured impedance signals may also be used for CPR treatment of the patient. For example, the impedance generally varies as the geometry of patient's chest changes due to the volume of air introduced, e.g., by a ventilation bag. By detecting the corresponding change in the impedance signal, a substantially accurate count of the ventilations may be determined along with other associated characteristics (e.g., ventilation rate, etc.). In some instances signals from the compression puck 108 (shown in FIG. 1) provided to the CPR feedback module 310 can be used in concert with the impedance signal to remove signal artifacts introduced during CPR treatment that may influence or even corrupt the impedance signal and thereby affect ventilation count accuracy and other quantities resulting in the patient being ventilated (e.g. over ventilated). By using this chest compression signal, the impedance signal may be processed to substantially remove artifacts that represent the chest compressions and thereby provide a more accurate count of the patient ventilations.

For another application, the measured impedance can be used to help determine when applying a shock to a person suffering from VF will be successful, i.e., will defibrillate the patient. Upon making such a determination, the defibrillator 104 may provide an indication to a rescuer about such a determination. For example, the defibrillator 104 may only allow a shock to be performed when the indication is sufficiently positive (e.g., over a set percentage of likelihood of success) as graphically displayed on the defibrillator so that the rescuer can determine whether to apply a shock.

The determination about likelihood of success for the patient receiving emergency care may employ a combination of the TTI impedance at one or more frequencies, ECG values at different frequencies or frequency ranges, etc. For example, quantities computed from ECG values (e.g., amplitude spectrum area (AMSA)) can be used to set a threshold for delivering defibrillation shock. The TTI can be used to adjust AMSA data to produce a more complete indication of whether a shock will succeed on the patient. Also, the TTI for the patient and the AMSA value may both be fed into a table or other form of function whose output can be used as a separate indicator of likely success.

Figure 5:
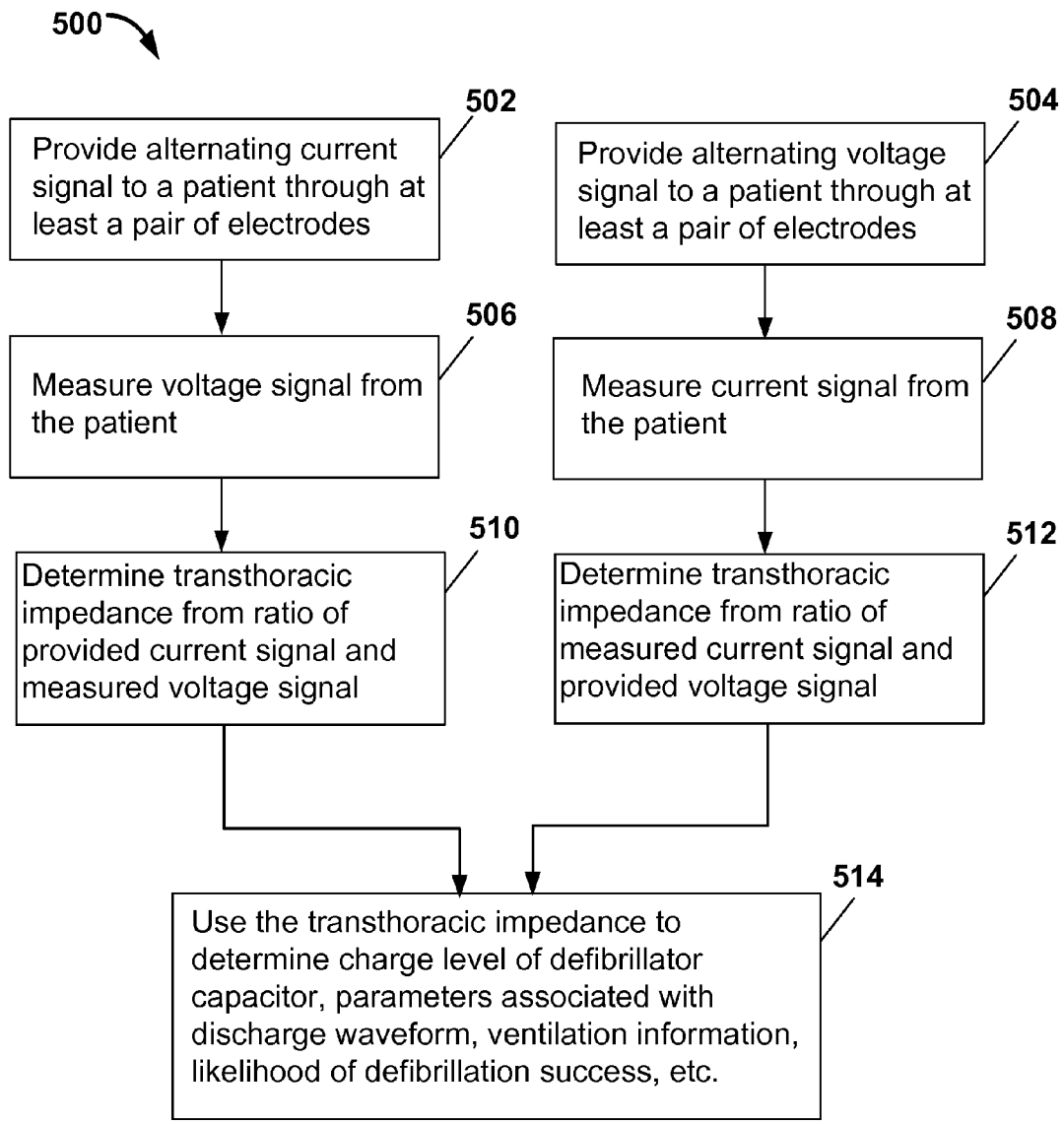
FIGS. 5 and 6 are flow charts of operations for determining and using the complex impedance of a patient.

Referring to FIG. 5, a flowchart 500 is shown that describes techniques for determining transthoracic impedance of a patient and using the impedance for a variety of applications, including defibrillator operations. For example, an alternating current signal (step 502) or an alternating voltage signal (step 504) may be provided to a patient through a pair of electrodes (or an array of electrodes that includes more than one pair). Based upon the provided signal, a voltage signal (step 506) or a current signal (508) can be measured by being sensed through the electrodes. Once measured, the complex transthoracic impedance can be calculated from the ratio of the provided signal and the measured signal (e.g., the ratio of the provided current signal and the measured voltage signal, step 510, or, the ratio of the provided voltage signal and the measured current signal, step 512). The transthoracic impedance can then be used (step 514) for determining one or multiple quantities. For example, the impedance can be used to select various voltage levels for charging the capacitor of a defibrillator, determine parameters associated with the discharge waveform (e.g., resistance levels, resistor schedules, etc.). The impedance may also be used for determining ventilation information associated with the patient (e.g., ventilation count, ventilation rate, etc.). For other applications, quantities such as the likelihood of defibrillation success may be determined from the impedance information, or the impedance information used in combination with other measures such as AMSA or other ECG signal measures.

The large signal impedance is a function of the defibrillation energy and the current density of the delivered defibrillation pulse. Thus lower energies will have higher defibrillation impedance compared to higher defibrillation energy waveforms. The optimal small signal frequency for estimating the impedance at a particular joule or current setting may be determined beforehand via experimental and clinical testing, and then the frequency chosen for measuring the small signal AC impedance can be chosen during operation based on the defibrillation joule or current setting of the defibrillator.

Alternatively, the small signal AC impedance may be calculated at two or more frequencies, wherein each frequency is an estimate for a range of defibrillation energy or current settings, e.g. 32 KHz may be used to estimate 10-100 joules, and 64 KHz may be used to estimate 100-400 joules (e.g., between 100-200 J, between 100-360 J). It may be possible to estimate other ranges of energy or current for various frequencies, for example, 32 KHz, 64 KHz or another suitable frequency may be used to estimate ranges of energy up to 2300 J. Alternatively, two or more values may be used to create an equation that may be used to calculate the expected impedance for a particular defibrillation energy or current setting. The equation may be linear or non-linear; it may involve best fit to experimental data using linear regression or spline fitting of data or other optimization means known to those skilled in the art. The information provided by the equation may alternatively be stored and retrieved in table form.

Figure 6:
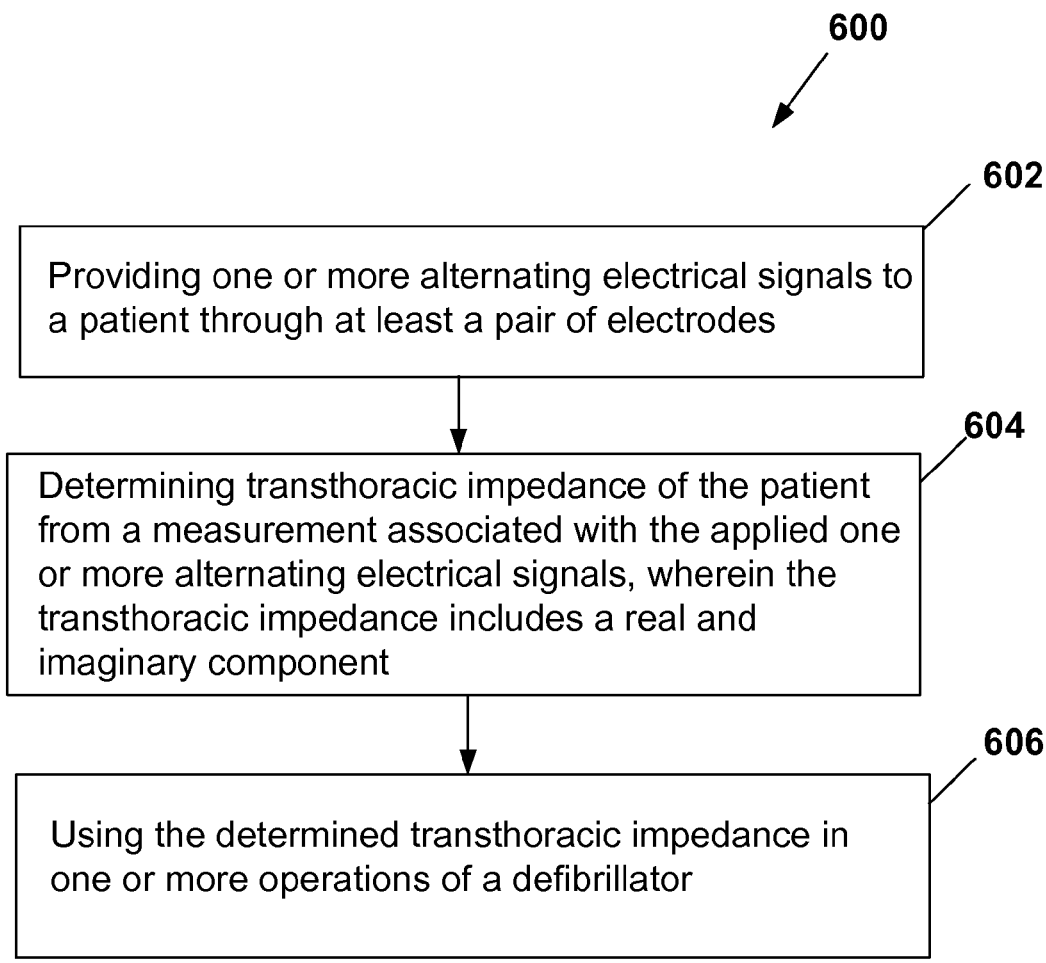

Referring now to FIG. 6, an example method 600 is shown for determining complex transthoracic impedance during the administering care to an individual requiring cardiac assistance. In one embodiment, the method 600 is implemented by the example defibrillators described above, however, other embodiments are possible.

At a step 602, one or more alternating electrical signals are provided to a patient through at least a pair of electrodes (e.g., the electrode package 106 shown in FIG. 2). For example, a series of sinusoidal current signals that cover a range of frequencies (e.g., within 10 to 100 kHz) may be provided by the defibrillator 104. While the frequencies of the signals may differ, other characteristics of the signals may be similar or different (e.g., similar or different phases, peak-to-peak amplitudes, etc.). In some arrangements, rather than employing multiple signals that each use a different frequency, one or a small number of signals (e.g., a chirp signal) that include a combination of different frequencies may be used. At step 604, the complex transthoracic impedance of the patient is determined from a measurement associated with the applied one or more alternating electrical signals. For example, the complex impedance (having a real and imaginary component) may be determined from the ratio of a measured voltage signal and the corresponding current signal applied to the patient. At step 606, the determined complex transthoracic impedance is used in one or more operations of a defibrillator. For example, the voltage level of the defibrillator capacitor may be selected, a parameter of a defibrillation waveform may be chosen (e.g., a resistor schedule selected to maintain a current level), etc. The complex impedance signal may also be processed for determining information associated with defibrillation, e.g., the impedance signal can be processed for monitoring respiratory activity (e.g., ventilation counts), determining likelihood of defibrillation success, etc.

In general, the current required for effective defibrillation is dependent upon the particular shape of the current waveform, including its amplitude, duration, shape (i.e., sine, damped sine, square, exponential decay), and whether the current waveform has a single polarity (monophasic) or has both positive and negative polarity (biphasic). However, it is worth noting that large defibrillation currents may cause damage to cardiac tissue.

Figure 7:
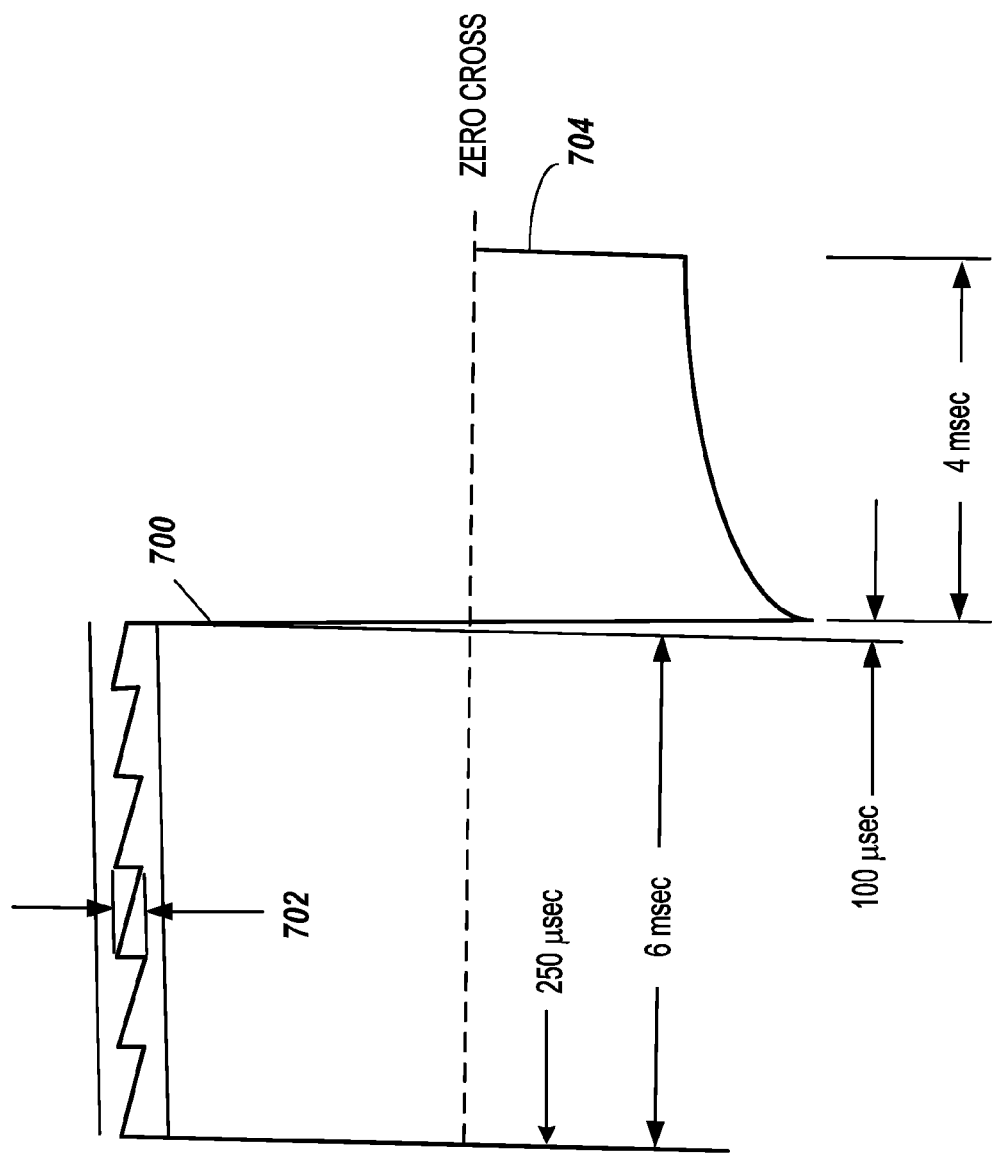
FIG. 7 is a diagram of an electrotherapy waveform.

Referring to FIG. 7, a current waveform is presented that can be employed by the defibrillator 104 being used by a rescuer caring for the cardiac arrest patient 102. In general, the defibrillator 104 can take various forms, for example, one such defibrillator may include the X Series defibrillator, from ZOLL Medical Corporation of Chelmsford, Mass. Other defibrillator implementations are also possible.

In this particular illustrated example, the biphasic current waveform is a rectilinear waveform. The biphasic defibrillation waveform includes a six-millisecond, generally rectilinear positive phase 700 having a sawtooth ripple 702, which is in turn followed by a four millisecond negative phase 704 that decays exponentially until the waveform is truncated.

A biphasic defibrillation waveform having a positive rectilinear pulse of 6 milliseconds duration followed by 0.1-millisecond transition and a 4 millisecond negative pulse having an initial amplitude equal to the final amplitude of the positive pulse is believed to be an especially effective waveform for defibrillation. In general, the negative pulse does not need to be rectilinear.

Figure 8:
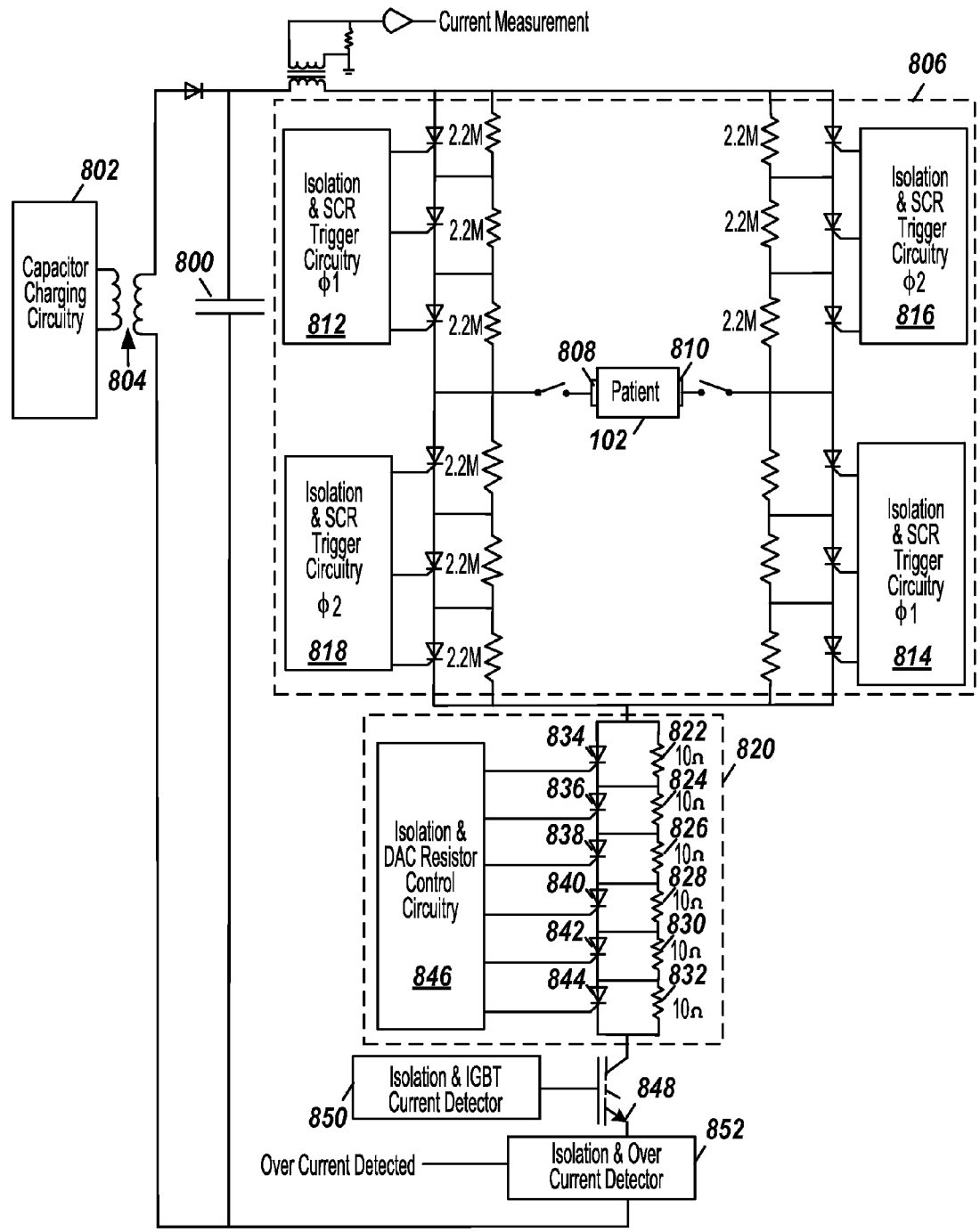
FIG. 8 is a diagram for providing an electrotherapy waveform to a patient.

Referring to FIG. 8, one type of circuit for producing the biphasic waveform is shown. A storage capacitor 800 is connected to charging circuitry 802 (via a transformer 804) that charges the capacitor to a voltage level while an H-bridge 806 is open. The electric charge stored in storage capacitor 800 is allowed to pass through electrodes 808 and 810 and the body of the patient 102. Triggering circuitry 812 and 814 of the H-Bridge 806 causes respective switches (e.g., SCRs) to close and allow current to pass through the patient's body in one direction, after which the transistor 848 causes the switches to open, and then trigger circuitry 816 and 818 causes respective switches (e.g., other SCRs) to close and allow the electric current to pass through the patient's body in the opposite direction. In some arrangements the trigger circuitry 812-818 is controlled by signals from a microprocessor (not shown) or one or more other types of processing devices. One or more switching devices (e.g., relays, SCRs, etc.) may be connected to the capacitor 800 and controlled by a processor (e.g., a microprocessor) to isolate patient 102 from leakage currents from the bridge 806, which may be considerable (e.g., 500 micro-amps). Such switching devices generally close a few milliseconds before the H-bridge 806 is "fired" by closure of some of the SCRs by the trigger circuitry 812-818 included in the H-bridge 806.

Electrodes 808 and 810 may be standard defibrillation electrodes having flat surfaces that adhere to the chest of the patient (for example a pair of electrodes may be adhered to a patient's torso—above one breast and below the other, for example, in a typical manner). In some arrangements, the electrodes 808 and 810 may alternatively be hand-held paddles that are applied to the chest of the patient or hand-held spoons that are applied directly to the patient's heart during a medical procedure (e.g., open heart surgery). Storage capacitor 800 may be a single capacitor, a combination of two or more connected capacitors (e.g., a set of series-connected or parallel-connected capacitors), etc. In some arrangements other types of energy storage devices may be employed with or without capacitor 800.

To dissipate excess energy stored in capacitor 800, a resistive network may be employed to control current being delivered to the patient. A resistive circuit 820 that includes six series-connected resistors 822, 824, 826, 828, 830 and 832 is provided in the current path, each of the resistors being connected in parallel with a corresponding shorting switch (e.g., an SCR) 834, 836, 838, 840, 842, and 844. While SCR devices can be employed for switching the resistors into and out of the circuit (based upon a selected resistor schedule), other types of devices may be used. For example, field-effect transistor (FET) technology, bipolar devices such as insulated gate bipolar transistor (IGBT) technology, etc. may be used in the circuitry. In this arrangement control circuitry 846 controls the operations of the shorting switches 834-844 and this circuitry may employ one or more techniques (e.g., microprocessor based circuitry to control the operations of the switches). As illustrated, each of the resistors have an equivalent resistance value (e.g., 10Ω), however, two or more of the resistors may have different resistance values in some implementations. For example, in one implementation, the resistors are of unequal value, stepped in a binary sequence to yield $2^n$ possible resistances where n is the number of resistors, etc. After the impedance of the patient 102 is measured (e.g., through the use of other circuitry, which can be processor based, etc.), the impedance can be used to determine a particular schedule of resistance values (for connected resistors 822-832) which may maintain a substantially constant voltage applied to the patient as voltage in the storage capacitor decreases during discharge, and which may further to track the decrease in voltage of the storage capacitor 800.

Along with the resistive circuit 820, an insulated-gate bipolar transistor (IGBT) 848 is operated by control circuitry 850 to turn off the bridge circuit when required. Additionally, a current detector 852 provides an alert signal if a particular current threshold is exceeded. This alert signal may be used by the control circuitry in 846 and 850 to reduce the flow of current when unexpectedly high currents are detected indicating a low patient impedance, sudden short circuit condition across electrodes 808 and 810, or under certain fault or device mis-use conditions.

Rather than using a large direct current signal to determine the impedance of a patient, one or more techniques may be employed. For example, measurements for determining impedance may be executed at multiple instances over a period of time (e.g., from placement of the electrodes 808 and 810 to defibrillation). To provide such measurements, circuitry may be utilized that may or may not employ a portion of the circuitry presented in FIG. 8. For example, the circuitry may provide a signal to the electrodes 808 and 810 (or another set of electrodes applied to the patient) at multiple time instances to attain multiple impedance samples over a period of time (e.g., between electrode placement and defibrillation). Once attained, one or more of the sampled impedances (e.g., the last impedance sampled before defibrillation, impedance sampled before or during charging of the capacitor, a statistical value calculated from the impedance samples, etc.) can be used to set multiple parameters associated with defibrillation. For example, along with setting the level of the charge storage device (e.g., one or more capacitors such as the capacitor 800), a schedule for introducing impedance for shaping the waveform may be selected from the determined patient impedance. Alternatively, multiple impedance measurements may be made at a number of different times (e.g. before starting capacitor charge, immediately before initiating discharge or during the previous or current discharge), which may be used for setting various parameters associated with the defibrillator.

Various types of signals may be employed for such impedance measurements. For example, an alternating electrical signal such as an alternating current (AC) signal of relatively low current (e.g., 100-350 micro amperes peak-to-peak) may be provided to the patient's body (via the electrodes 810 and 812) by a circuit which may or may not employ a portion of the circuit presented in FIG. 8. While the same pair of electrodes may be used to introduce both the defibrillation shock and the AC signal, in some arrangements, a separate pair of electrodes may be employed for application of the AC signal. To determine patient impedance, the voltage present across the patient (e.g., the electrodes 810 and 812) may be measured and the impedance calculated. In a somewhat similar system, an AC voltage signal of relatively low voltage may be provided to the patient's body (e.g., via the electrodes 810 and 812) by a circuit (that may or may not use a portion of the circuit in FIG. 8). With the voltage applied, the current flow through the patient's body may be measured and the corresponding impedance calculated (e.g., based upon Ohm's law). Other types of measurements may also be employed for determining impedance. For example, voltage or current decay can be measured over a period of time for a charge present on a capacitor (such as storage capacitor 800). From the known capacitance of the storage capacitor, the impedance can be calculated from the measured decay.

In some arrangements, multiple measurement techniques may be used in concert to determine patient impedance. For example, impedance may be determined using a high voltage signal from the storage capacitor 800 and from introducing a low current (or voltage) signal, such as a low current AC signal. Using impedance data attained from both techniques, one or more processes may be executed (e.g., calculate an estimated value, variance, standard deviation, etc.) to arrive at an impedance value for the patient's body using both data sets, which can then be used for selecting parameters such as the voltage level of the storage capacitor and the resistor schedule. In one application, the difference between impedance levels measured by different techniques (e.g., two different techniques) may be utilized. For example, the difference of impedances measured from a high voltage DC signal and a high frequency AC can be determined and used to indicate how well defibrillator electrodes are coupled to a patient. Once determined, an alert or other type of indication may be produced (e.g., by the defibrillator) to inform the rescuer when marginal, improper, etc. electrode contact is suspected. In alternative embodiments, high frequency AC measured impedance may be used to set defibrillation parameters, although inconsistencies between successive measurements over the period immediately prior to defibrillation may arise. This inconsistency might occur if electrodes are not suitably connected to the patient. In such an instance, the impedance measured at other recent times may be use to set the defibrillation parameters. For example, a metric that represents consistency between two or measurements can be calculated, and upon determining that the metric fails to satisfy a threshold condition, a previously measured impedance value may be used in place of the inconsistent measurements. Recent measurements may include high frequency AC measurements made before or during capacitor charging, high voltage DC impedance measurements made during the previous defibrillation, or a default value (such as 50 ohms) may be used when no consistent or previous high voltage measurements are otherwise available.

Comparatively, the amplitude of the AC current signal can be considerably less than the high voltage amplitude. Along with the lower signal amplitude having less of an effect on the physiology of the patient's body, other characteristics of the AC current signal may reduce the physiological effects of the applied signals. In general, a relatively high frequency signal may have less physiological effects compared to a direct current signal. The frequency of the AC current signal would typically be selected from a range (e.g., 10 to 200 kilo Hertz (kHz)) such as 31 kHz or another frequency. In some arrangements, other signals parameters (e.g., phase, modulation technique, etc.) may be employed by the AC signal for impedance measurements that have little or no physiological effects on the patient's body.

By not being restricted to high voltage signal from the storage capacitor, impedance measurements may be executed more frequently and over various periods of time, thereby adding more flexibility and accuracy to the impedance measurements. Additionally, the impedance measurements are not restricted to using the discharge of the storage capacitor as a source, which can take 10 s of seconds to charge. Along with potentially executing impedance measurements over an extended period of time, multiple measurements may be performed from the time that electrodes are positioned upon the patient's body to the initial application of the defibrillation discharge. During of this time period, which can be hundreds of milli-seconds in length, a number of individual impedance measurements (e.g., 2, 6, 10, etc.) can be performed.

Along with providing flexibility in measurement timing, the use of such high frequency—low current signals also reduces the probability of some safety concerns. For example, arching from the electrodes to the patient's body is considerably less probable using such low current signals (e.g., 100 to 350 micro amps) rather than larger current signals (e.g., 10 amps) from the discharge capacitor (e.g., storage capacitor 800). Arching from such high current signals can also become more likely due to the placement of the electrodes. For example, a considerably hairy chest (of a patient) can cause an arch-inducing gap to be formed (between the patient's skin and the electrode). As such, a low current signal can further reduce the likelihood of potentially dangerous electrical discharges in such situations. Further, as mentioned above, by using two techniques to measure impedance (e.g., a large DC signal and a high frequency AC signal), impedance measurements may be compared to determine integrity of the electrode positioning with respect to the patient's skin.

Similar to using one signal at multiple time instances (e.g., introducing a high frequency, low amplitude AC signal at multiple times), signals with different characteristics may be employed to attain information about the transthoracic impedance of a patient. For example, the AC signal may be generated by a voltage source and then a current measurement circuit can be employed for measurements for calculating impedance; or alternatively, the AC signal may be generated by a current source and measurements from a voltage measurement circuit can be used to calculate impedance. Signals having different characteristics (e.g., phase, frequency, etc.) may be introduced (via electrodes) to the patient's body. Through these different signal characteristics, additional information may be attained for accurately estimating impedance. By applying signals that each have a different frequency (e.g., two or more predefined frequencies), or a range of frequencies (e.g., a chirp signal), etc., impedance spectroscopy techniques may be employed to measure and quantify complex impedance components (e.g., resistance and reactance) as provided by the ratio of applied AC current signals and correspondingly measure voltage signals. Through the collection of such real and imaginary data, additional information can be gathered to reflect changes in impedance that are experienced at different frequencies.

Using relatively small AC signals in such measurements, on the order of 100 to 350 micro amperes, as typically used in embodiments of this invention, transthoracic impedance values may appear non-linear over frequency (e.g., due to ionic migration from the electrolytes present in the patient's body). The frequency ranges typically employed in embodiments of this invention are 10 Hz-200 kilohertz. Update rate for estimation of transthoracic impedance is at least 0.1 Hz. Additionally, other types of frequency dependent artifacts may be present (e.g., due to the electrodes, current density of applied signals, etc.). By employing impedance spectroscopy techniques, complex impedance (or conductivity) data can be collected (e.g., over a range of frequencies, phases, etc.) to produce a representation (e.g., a numerical model) of the patient's impedance. In one example, poles and zeros of a transfer function representation can be determined from the measured complex impedance data. Other types of representations may be employed for representing the complex impedance, for example, an equivalent circuit (e.g., that includes resistive, capacitive, inductive elements, etc.) can provide meaningful properties by modeling the frequency dependent impedance data. In some arrangements, measurements involving other variables are carried out to include more information for characterization; for example, impedance measurements may be performed over a range of temperatures or other externally controlled experimental variables. Such impedance measurements may employ different types of circuitry, defibrillator equipment, etc. For example, frequency response analyzer circuitry can be utilized by a defibrillator for imposing small amplitude AC signals along with circuitry for collecting and analyzing the responsive voltage or current signals to determine resistive, capacitive and inductive behavior of the impedance for the frequency of the signal. Microprocessor based techniques may also be employed for performing such operations.

Once measured, the complex impedance values can be processed (e.g., averaged, weighted, filtered, etc.) to determine one or more quantities (e.g., charge level of the storage capacitor, resistor schedule, etc.). Transfer functions, equivalent circuit models, etc. may also be developed from the complex impedance data for computing desired quantities. In some arrangements, representations of the complex impedance values may be employed for making determinations. For example, the values may be represented in a Bode plot to provide impedance magnitude (or the real or imaginary components of the impedance) and phase angle as a function of frequency. Since the impedance and frequency can span orders of magnitude, data can be logarithmically scaled for such plots. Imaginary impedance, which is indicative of capacitive and inductive characteristics, can be represented versus the real impedance components in representations (Nyquist plots). Represented for one particular frequency, impedance is provided as a vector quantity (e.g., magnitude and phase angle) and can also be employed for defibrillator operation (e.g., parameter selections, etc.). Other impedance spectroscopy operations and processing techniques of complex impedance may be employed as provided by "Impedance Spectroscopy, Applications to Electrochemical and Dielectric Phenomena" by Vadim Lvovich, A John Wiley & Sons, Inc. Publication, July 2012, which is incorporated by reference herein in its entirety.

Figure 9:
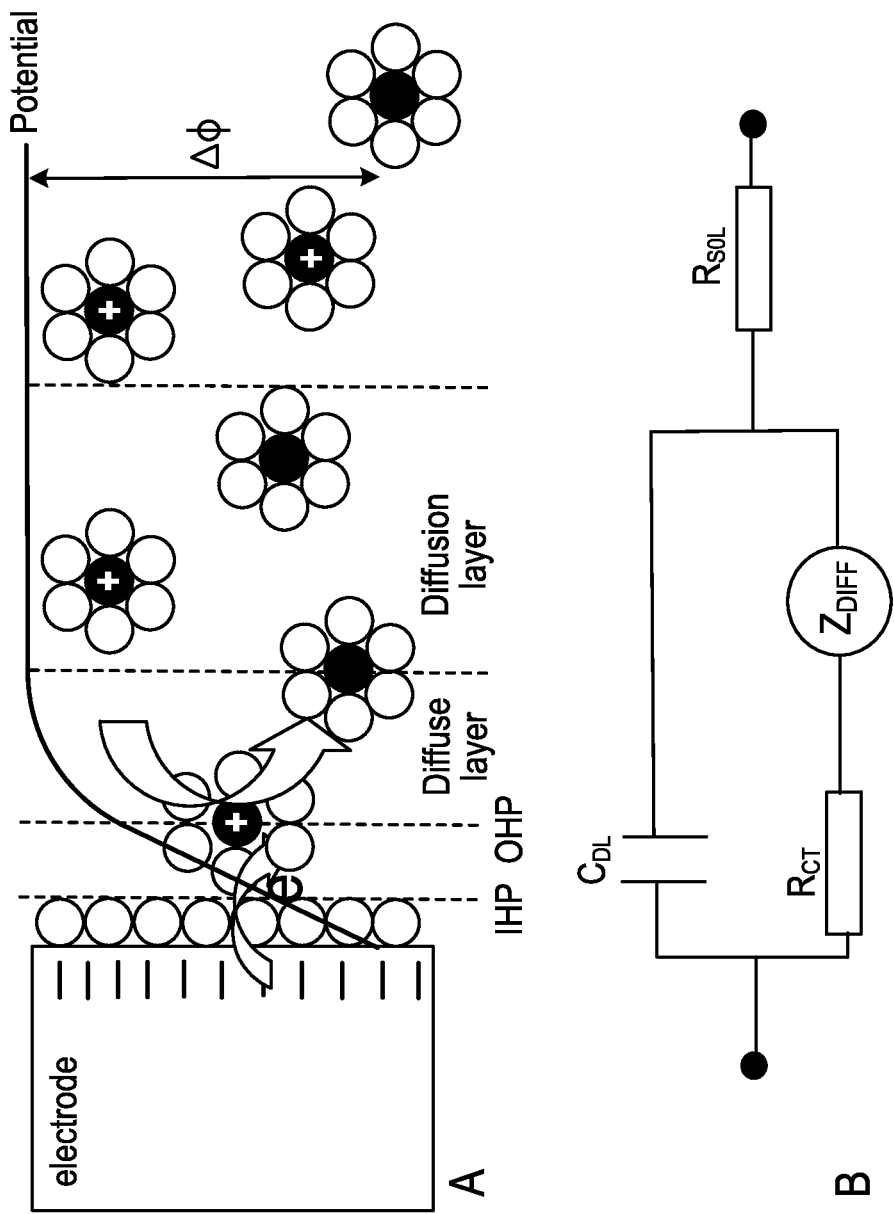
FIG. 9 is a diagram representing interfacial electrochemical reactions and an electrical circuit.

For instance, the electrode-electrolyte-skin (EES) interface may be modeled as lumped circuit elements as shown in FIG. 9. The impedance of the physiologic tissue—the skin/blood/lung/adipose/myocardial tissue—can then be analyzed separately on a continuous and real time basis. The double-layer capacitance, $C_{DL}$, is highly sensitive to pressure or pulling, such as what occurs during the course of chest compressions during cardiopulmonary resuscitation. By providing an estimate of $C_{DL}$, it can be used as the adaptive reference signal in an adaptive filter, such as an ARMA filter, e.g. Kalman, or other adaptive noise cancelling filter like a particle filter, in order to remove the artifact injected into the electrically-based physiologic (EBP) signals. Such EBP signals are any physiologic signals measured on the body one of whose inputs are based on measuring either current or voltage (or both). Examples of such signals are ECG, EEG, impedance pneumography, impedance cardiography, impedance tomography, though not limited to this list. Additionally, one or more of the other lumped circuit elements from the estimated lumped model of the EES interface may be used for adaptive filtering of EBP signals. Further, the lumped circuit model may include specific elements for patient's impedance. This patient impedance may be further characterized by including specific lumped elements representing the skin, heart, lungs or other organs of interest. Based on the more reliably estimated organ impedance using this method, ventilations and spontaneous breathing as well as the blood volume shifts in the aorta and chambers of the heart can be measured and displayed under a broader range of real-world conditions, such as during chest compressions or with significant ambulatory motion of the patient, as is often encountered in pre-hospital medical care and emergency conditions. As a result, the spontaneously beating heart can be detected during chest compressions without having to stop compressions to check a patient's pulse. This can be important because even pausing compressions for as short as 5 seconds during CPR has been shown to have serious deleterious consequences on patient survival.

In some versions of the invention, there may be more than two electrodes, such as what is used with electrical impedance tomography (EIT), well known to those skilled in the art, that may use as many as 64 electrodes covering a surface area of interest, so that the three dimensional map of organ impedances can be estimated. More accurate impedance tomographs may be created by estimating the lumped circuit model for the EES interface of all the electrodes in real time of the EIT system.

The amplitude of the AC impedance-measuring signal may be amplitude modulated so as to be able to further characterize the battery-like, half-cell potential characteristics of the electrode-electrolyte-skin (EES) interface, thus further enhancing the accuracy of the impedance measurement. The amplitude modulation signal may take the form of a trapezoid of approximately 10 milliseconds. The amplitude of the AC signal, at the start of the trapezoidal amplitude modulating ramp will be at the small signal amplitude, as discussed above, of approximately 1-5 microamperes. At the end of the trapezoidal ramp, the amplitude will have increased to as much as 100 milliamps. Since the capacitive elements of the EES interface dominate at the higher frequencies, the amplitude modulating testing is performed preferably at slightly lower frequencies, such as in the range of 10 Hz-1 kHz. The trapezoidal pulses may be concatenated so as to create a continuous or near-continuous train of pulses creating a sawtooth amplitude modulation effect, with each pulse of a different frequency, therefore making it possible to generate the spectroscopic impedance measure in real time. The frequency may also be modulated simultaneously with the amplitude modulation, thus creating a frequency modulated "chirp" signal, the amplitude of the pulse also increasing over the course of the pulse.

Once determined, the impedance may be used for one or more defibrillator operations. For example, an impedance value determined from multiple values (e.g., an estimated value calculated from periodic impedance measurements) or a single impedance value (e.g., determined just prior to defibrillation) may be employed to estimate the patient body's impedance likely to be encountered during defibrillation. A target voltage level for the storage capacitor (or capacitors) can be determined from defibrillator energy to be delivered (e.g., selected, predefined, etc.), the impedance value, and anticipated energy dissipation (e.g., energy loss internal to the defibrillator). An impedance value determined from a measurement (or multiple measurements) performed just prior to the start, completion, etc. of capacitor charging may be employed to set the voltage level. However, in other arrangements, an impedance value attained (from one or multiple measurements) prior to one defibrillation may be used for setting a target voltage for one or more subsequent defibrillations.

Along with setting the voltage level of the storage capacitor, other parameters associated with defibrillation may be determined from the attained impedance value. For example, the determined impedance can be used to select a schedule for applying resistance values (e.g., via the resistors 822-832, the resistor-shorting switches 834-844) to control the shape of the defibrillation waveform (e.g., illustrated in FIG. 7). Resistors are selected (as provided by the schedule) such that a generally flat current is provided during the first phase of the waveform (as the voltage level of the storage capacitor decreases). Resistance values may also be introduced to maintain a substantially constant resistance. For example, if the patient's impedance appears to fluctuate over time (as determined from multiple impedance measurements) different resistance values may inserted in series with the patient impedance to maintain a desired overall impedance level. For example, more resistance may be inserted if the patient impedance drops, or resistance may be removed for the situation in which the patient impedance increases.

As described below, resistance values may be introduced in steps for a variety of situations. For example, an initial resistance (to be provided by one or more of the resistors) may be identified from the measured impedance value. In general, for patient bodies with low measured impedance, a considerable amount of resistance can be placed in series (e.g., through operation of the switches such as switches 834-844). Alternatively, for bodies with relatively large measured impedance, a lesser amount of resistance is connected in series with the patient. Other portions of the current waveform, illustrated in FIG. 7, may also be controlled through the determined impedance, such as controlling the duration of different portions of the current waveform. For example, along with controlling the duration of the first phase of the current waveform, the duration of the second phase of the current waveform may be adjusted through use of impedance measurements.

Figure 10:
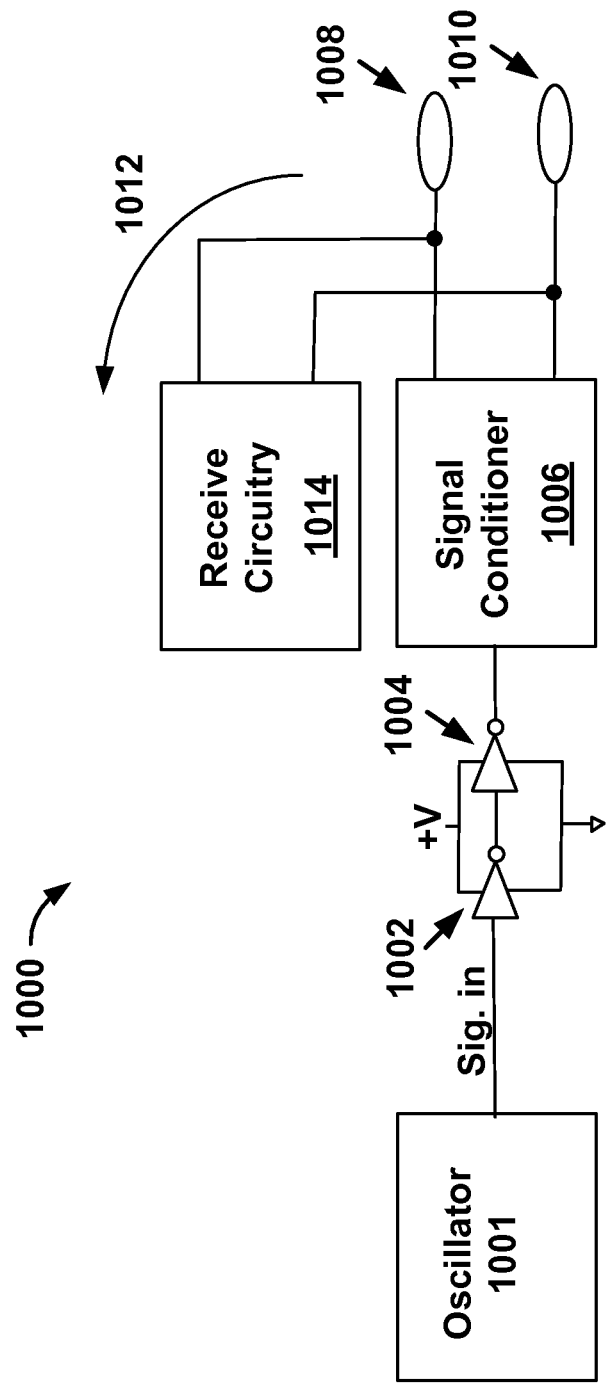
FIG. 10 is a block diagram for producing a relatively small alternating current signal for patient impedance measurements.

Referring to FIG. 10, circuitry 1000 is presented that is capable of producing a relatively high frequency alternating electrical signal (e.g., an AC signal) for measuring the impedance of a patient through a pair of electrodes. The alternating electrical signal can be generated using an oscillator 1001. A drive signal (sig. in) from the oscillator 1001 is provided to two inverters 1002 and 1004 connected in series. The drive signal in may be appropriately amplified or otherwise conditioned. Once produced and conditioned (e.g., by a signal conditioner 1006), the AC signal is provided to a pair of electrodes 1008 and 1010 placed upon the patient (e.g., via paddles). In this example, an AC current signal applied, and a voltage signal is sensed and collected by the electrodes and provided (as represented with arrow 1012) to receive circuitry 1014 (e.g., a multi-channel multiplexer and amplifier/filter package) for producing a signal that a processor (e.g., such as a microprocessor) can use to quantify the impedance of the patient. FIG. 10 provides one exemplary circuit capable of producing a low current, high frequency signal for delivery to measure patient impedance. Other types of circuitry, which may or may not employ portions of the circuitry 1000, may be incorporated into an external defibrillator to prepare and deliver such signals for impedance measurements.

Figure 11:
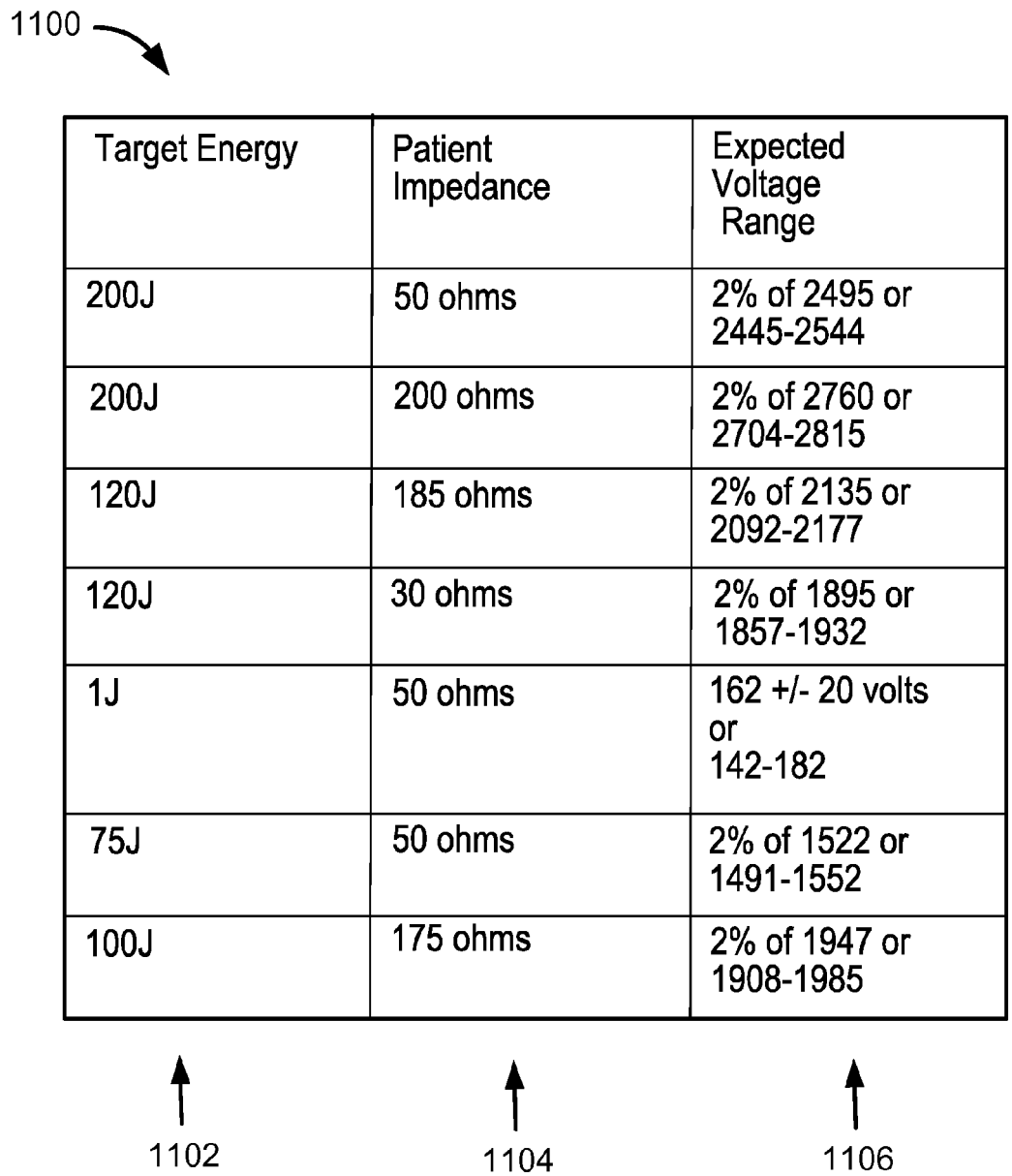
FIG. 11 presents a table of charge storage device voltages for different energy levels and patient impedances.

Referring to FIG. 11, based upon the impedance value attained from the AC signal measurements, various voltage levels for charging the charge storage device (e.g., capacitor, capacitors, etc.) may be identified. A table 1100 presents voltage level selections based upon the impedance measured from a patient of interest and the energy level selected for defibrillation (e.g., 200 Joules (J), 120 J, 100 J, 75 J and 1 J), as represented in the left-most column 1102 of the table. Along with the selectable energy level, the table provides in column 1104 example patient impedances that include 200Ω to 185Ω, 175Ω, 50Ω, and 30Ω. While the column 1104 provides a list of example resistance values, other resistance values may be similarly utilized. Based upon the target energy level and the patient impedance, a target voltage range can be calculated (as represented in column 1106). Such voltages ranges can be calculated from one or more equations that use the patient impedance and the selected target energy. In general, the target voltage range can be considered as providing the voltage level needed to set the charge storage device for the target energy level (represented in column 1102).

Various techniques may be utilized to identify such voltage levels from the selected energy and patient impedance. For example, one or more database, data processing, data storing, etc. techniques may be employed to determine the desired voltages from the selected energy level and patient impedance. For example, a processor (e.g., microprocessor) included in the defibrillator may be provided data representing the selected energy level and determined patient impedance. By accessing one or more equations, tables, relational databases, data files, etc., and performing associated operations, etc., one or more appropriate voltage levels (e.g., represented in table 1100) may be identified for use by the defibrillator.

Along with determining one or more appropriate voltage levels for charging the charge storage device (e.g., capacitor, capacitors, etc.) of the defibrillator, the impedance of the patient (as provided from the high frequency, low current AC signal) may be utilized to identify the appropriate resistor schedule for defibrillator operations. Referring to FIG. 12, a table 1200 is presented that provides a predefined resistor schedule for the energy level selected (e.g., manually or automatically) to be administered to the patient (as provided by column 1202). Along with the energy setting, column 1204 provides the target voltage to attain the desired energy level represented in column 1202. Eight ranges of patient impedance (e.g., 0-23Ω, 24-40Ω, 41-65Ω, 65-115Ω, 116-135Ω, 136-160Ω, 161-185Ω and 185-205Ω) as provided by columns 1206-1220. While eight ranges of these particular resistances are presented, more or less ranges may be utilized along with other resistance ranges. For each resistance range, six resistance values are presented for most energy setting (five values are provided in columns 1210 and 1212 for the 200 J setting). The six values identify the amount of resistance to be inserted into the circuit shown in FIG. 8 for a period of time (e.g., for the 10 milli-second time period of the two phases illustrated in FIG. 7). For each schedule, the resistance level starts at a relatively high level (e.g., 60Ω, 50Ω, etc.) and generally reduces across the five subsequent values. To provide the resistance values, corresponding resistors (e.g. resistors 822-832 shown in FIG. 8) are connected or shorted across (e.g., by the respective SCRs 834-844 also shown in FIG. 8). For example, for resistance values of 0Ω each of the resistors is shorted across and for other values only a portion of the resistors are shorted (e.g., to provide 40Ω of resistance, two of the 10Ω resistors are shorted across and the remaining four 10Ω resistors remain connected in series). While six time segments are employed in the illustrated example, more or less segments may be included in a schedule. The length of the individual segment may also be adjusted; for example, rather than having segments used for equivalent lengths of time (e.g., a length of 1.2 ms, 1.5 ms, 2.0 ms, etc.), one or more schedules may be defined with multiple segments having different time lengths. Other types of adjustments may also be implemented; for example, rather than each schedule having equivalent segments (e.g., six segments), some schedules may have more (e.g., seven, eight, etc.) or less (e.g., four, three, etc.) segments. In some arrangements more or less resistor schedules may be utilized. For example, multiple resistor schedules may be employed in some arrangements based upon an energy level and patient impedance. For example, two or more schedules may be combined (e.g., one appended to another), interleaved, etc. prior to being employed by the defibrillator.

Figure 13:
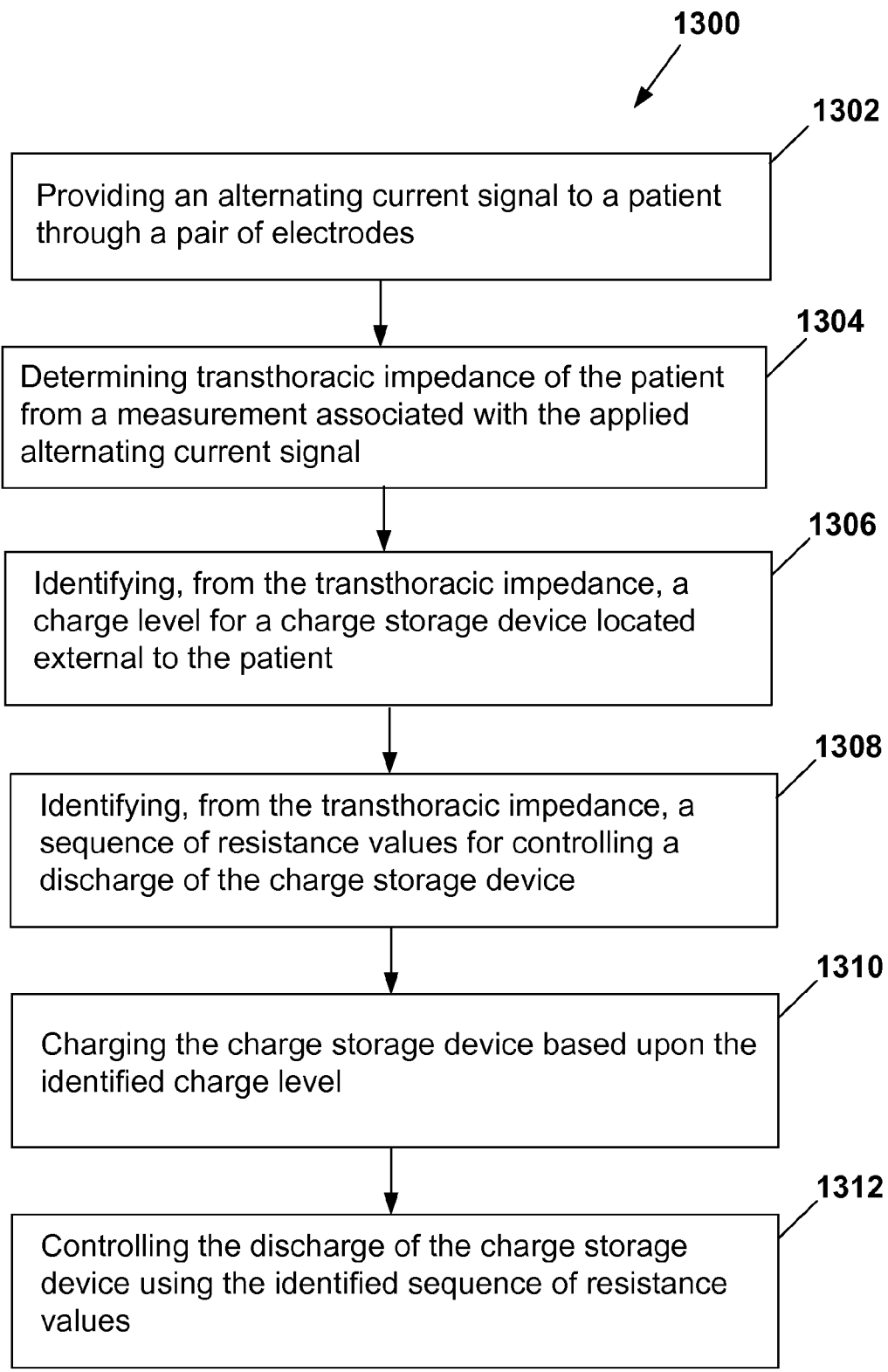
FIGS. 13 and 14 are flow charts of operations for using patient impedance for selecting waveform parameters.

Referring now to FIG. 13, an example method 1300 is shown for administering care to an individual requiring cardiac assistance. In one embodiment, the method 1300 is implemented by the example defibrillators described above, however, other embodiments are possible.

At a step 1302, an alternating electrical signal is provided to a patient through at least a pair of electrodes (e.g., electrodes 808 and 810 shown in FIG. 8). The frequency of the alternating electrical signal (e.g., a current signal, a voltage signal, etc.) is typically within a range of 10 to 100 kHz (e.g., 31 kHz) and has a relatively low peak-to-peak amplitude. At step 1304, the transthoracic impedance of the patient is determined from a measurement associated with the applied alternating electrical signal. For example, the impedance may be determined from the voltage measured from an AC current signal applied to the patient, or, impedance may be determined from the current of an AC voltage signal applied to the patient (e.g., across an electrode pair). At step 1306, a charge level for a charge storage device located external to the patient is identified from the determined transthoracic impedance. For example, based upon the impedance and the energy (in joules) to be delivered to the patient, the charge level may be determined (e.g., from one or more tables, equations, relational databases, etc.). Along with this charge level selection, a second parameter can be selected for producing an appropriate waveform (as illustrated in FIG. 1). In some embodiments, the second parameter may be selected based upon a more recent impedance measurement taken after charging is completed. This may be advantageous when paddles are in use and only applied to the patient after charging is complete. In this case, the charge level of the capacitor may be determined by either the impedance measured during the previous defibrillation or by use of a default value if no prior patient impedance information is otherwise available. At step 1308, a sequence of resistance values can be identified from the transthoracic impedance for controlling a discharge of the charge storage device. For example, one or more resistance schedules represented in FIG. 12 can be selected based upon the impedance determined from the high frequency, low current signal(s) introduced to the patient. In some arrangements, the operations performed at step 1306 or step 1308 may be considered optional. For example, in some arrangements only one parameter (e.g., the charge level of the charge storage device or the resistance value sequence) may be identified from the transthoracic impedance. At step 1310, from the identified information action is taken; for example, the charge storage device is charged based upon the identified charge level. For example, circuitry, executed operations, a combination or hardware and software, etc. may be employed by a defibrillator for charging the storage device to the identified level. At step 1312, the discharge of the charge storage device is controlled using the identified sequence of resistance values. For example, circuitry (e.g., the circuitry shown in FIG. 8) may be used for introducing and removing resistance values based upon a selected resistor schedule to substantially maintain a current level, a resistance value (due to changes in patient impedance), etc. for defibrillating the patient.

Figure 14:
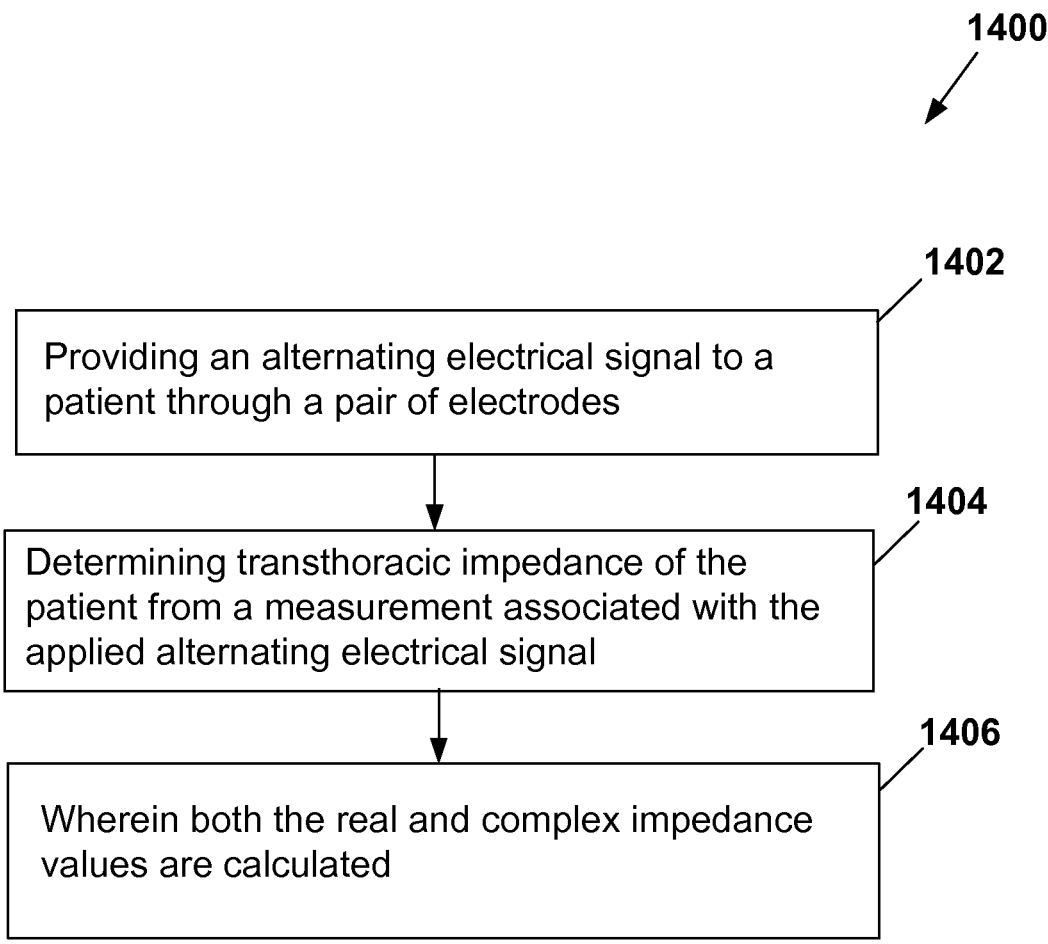

Referring now to FIG. 14, an example of another method 1400 is shown for administering care to an individual requiring cardiac assistance. In one embodiment, the method 1400 is implemented by the example defibrillators described above, however, other embodiments are possible.

At a step 1402, an alternating electrical signal is provided to a patient through at least a pair of electrodes (e.g., electrodes 810 and 812 shown in FIG. 8). As mentioned above, the frequency of the alternating electrical signal (e.g., a current signal, a voltage signal, etc.) can be within a range of 10 to 100 kHz (e.g., 31 kHz). Further, the alternating electrical signal typically has a relatively low peak-to-peak amplitude. At step 1404, the transthoracic impedance of the patient is determined from a measurement associated with the applied alternating electrical signal. For example, as described above, the impedance may be determined from the voltage measured from an AC current signal applied to the patient, or, impedance may be determined from the current of an AC voltage signal applied to the patient (e.g., across an electrode pair). At step 1406, both real and complex impedance values are calculated for the transthoracic impedance of the patient from the measurement of the alternating electrical signal. For example, impedance spectroscopy techniques may be employed to calculate complex impedance values from the measurement data. Once calculated, the complex impedance may be used in defibrillator operations such as setting charge levels and selecting resistor schedules.

Figure 15:
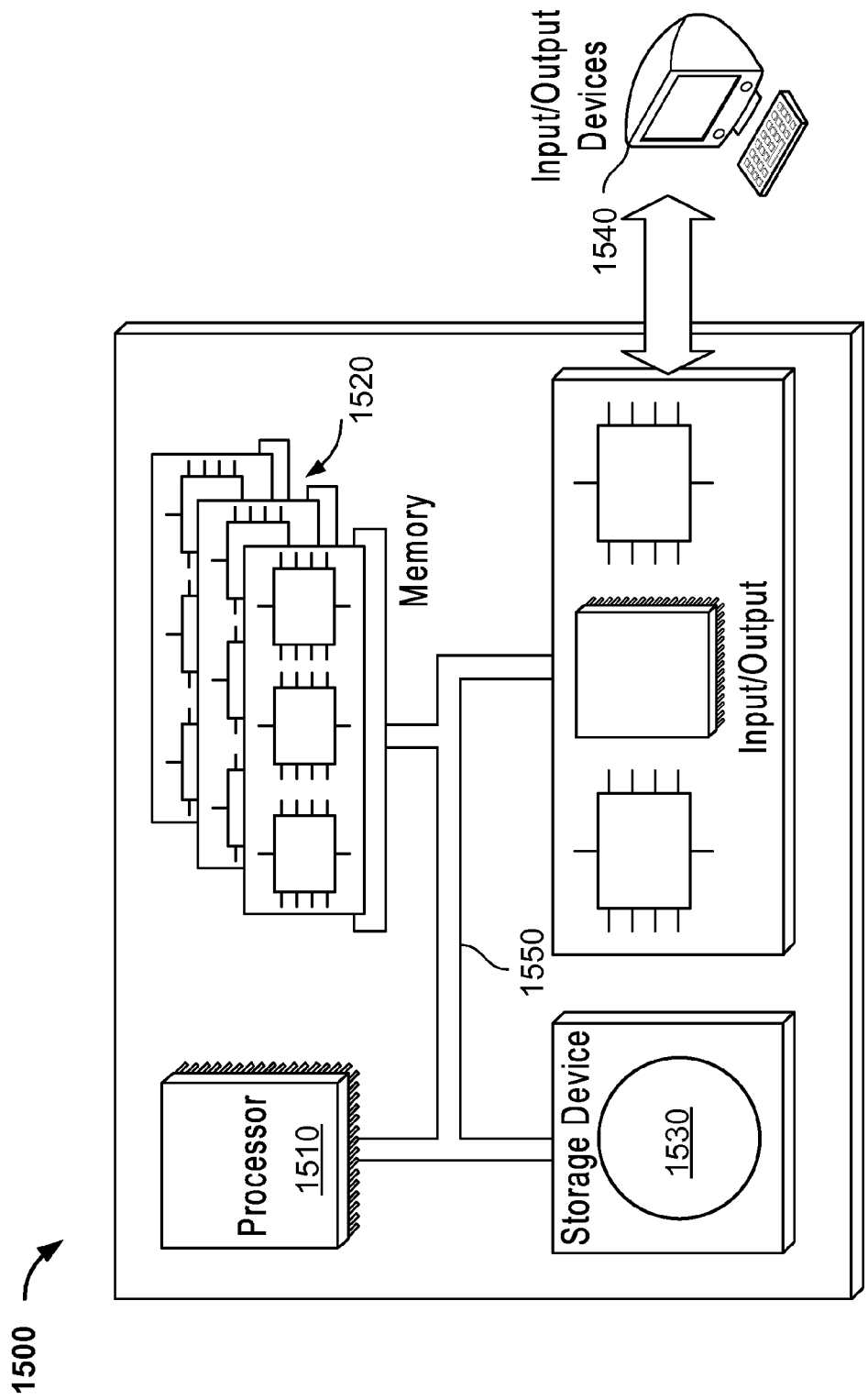
FIG. 15 shows an example of a generic computing device, which may be used with the techniques described here.

The particular techniques described here may be assisted by the use of a computer-implemented medical device, such as a defibrillator that includes computing capability. Such a defibrillator or other device is shown in FIG. 15, and may communicate with and/or incorporate a computer system 1500 in performing the operations discussed above, including operations for determining patient impedance from one or more high frequency, low current signals and selecting two or more parameters (e.g., amplitude and resistance schedule). The system 1500 may be implemented in various forms of digital computers, including computerized defibrillators laptops, personal digital assistants, tablets, and other appropriate computers. Additionally, the system can include portable storage media, such as Universal Serial Bus (USB) flash drives. For example, the USB flash drives may store operating systems and other applications. The USB flash drives can include input/output components, such as a wireless transmitter or USB connector that may be inserted into a USB port of another computing device.

The system 1500 includes a processor 1510, a memory 1520, a storage device 1530, and an input/output device 1540. Each of the components 1510, 1520, 1530, and 1540 are interconnected using a system bus 1550. The processor 1510 is capable of processing instructions for execution within the system 1500. The processor may be designed using any of a number of architectures. For example, the processor 1510 may be a CISC (Complex Instruction Set Computers) processor, a RISC (Reduced Instruction Set Computer) processor, or a MISC (Minimal Instruction Set Computer) processor.

In one implementation, the processor 1510 is a single-threaded processor. In another implementation, the processor 1510 is a multi-threaded processor. The processor 1510 is capable of processing instructions stored in the memory 1520 or on the storage device 1530 to display graphical information for a user interface on the input/output device 1540.

The memory 1520 stores information within the system 1500. In one implementation, the memory 1520 is a computer-readable medium. In one implementation, the memory 1520 is a volatile memory unit. In another implementation, the memory 1520 is a non-volatile memory unit.

The storage device 1530 is capable of providing mass storage for the system 1500. In one implementation, the storage device 1530 is a computer-readable medium. In various different implementations, the storage device 1530 may be a floppy disk device, a hard disk device, an optical disk device, or a tape device.

The input/output device 1540 provides input/output operations for the system 1500. In one implementation, the input/output device 1540 includes a keyboard and/or pointing device. In another implementation, the input/output device 1540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier (e.g., in a machine-readable storage device for execution by a programmable processor) and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks (such as internal hard disks and removable disks), magneto-optical disks, and optical disks. Storage devices suitable for tangibly embodying computer program instructions and data include all forms of non-volatile memory, including by way of example semi-conductor memory devices (such as EPROM, EEPROM) and flash memory devices, magnetic disks such as internal hard disks and removable disks, magneto-optical disks, and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user, a keyboard, and a pointing device such as a mouse or a trackball by which the user can provide input to the computer.

The features can be implemented in a computer system that includes a back-end component (such as a data server) or a middleware component (such as an application server or an Internet server), or a front-end component (such as a client computer having a graphical user interface or an Internet browser), or any combination of them. The components of the system can be connected by any form or medium of digital data communication, such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Figure 16A:
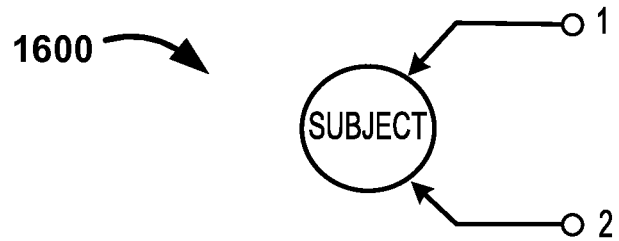
FIG. 16A shows a block diagram of a patient's tissue and electrodes.
Figure 16B:
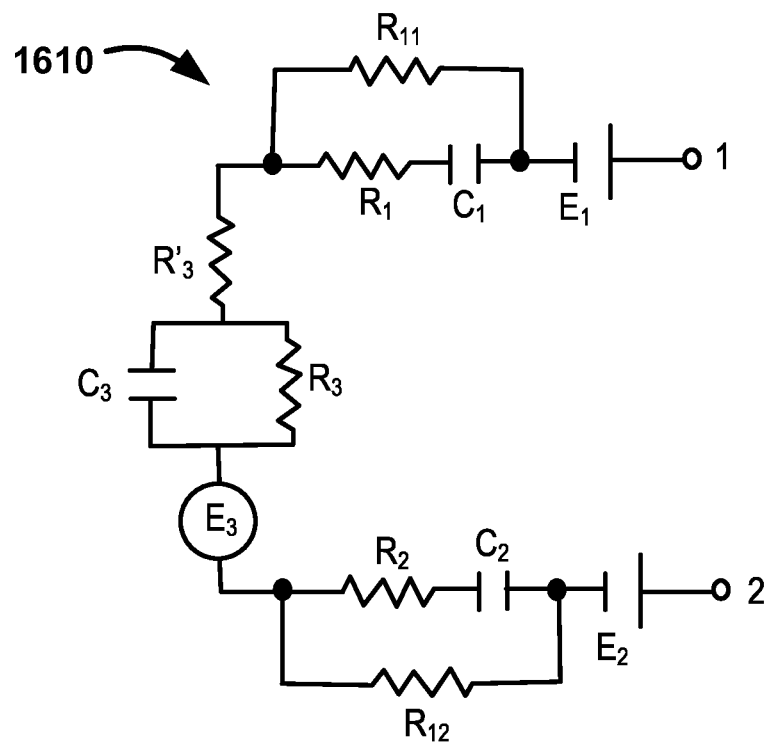
FIGS. 16B and 16D show circuit models of a patient's tissue and electrodes.
Figure 16C:
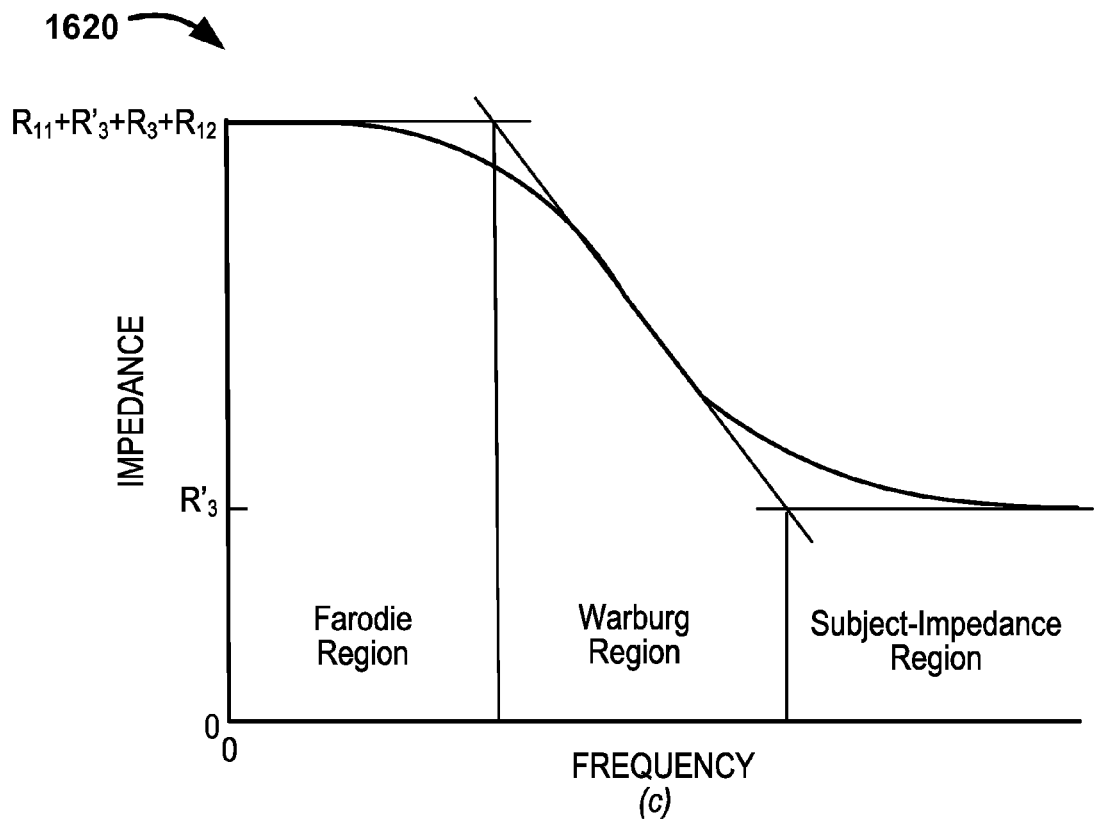
FIG. 16C shows a graph of frequency response of the circuit model of FIG. 16B.

As noted above, tissue impedance generally decreases with an increase in frequency. A circuit model can be used to represent the combination of a patient's tissue (e.g, a patient's chest, a patient's organs, etc.) and electrodes applied to the patient's skin. FIG. 16A-16B show an example of a block diagram 1600 and a circuit model 1610 of a pair of electrodes in contact with a patient generating and/or sensing an electrical signal in the patient's body (e.g., sinusoidal voltage signal). The circuit model 1610 includes electrode terminals (1,2), two half-cell potentials ($E_1$, $E_2$), two electrode-patient impedances ($R_1$, $C_1$, $R_{f1}$ and $R_2$, $C_2$, $R_{f2}$), a circuit representing the patient ($R_S$, $C_S$, $R_S'$), and the bioelectrical signal $E_b$ (e.g., a signal representing electrical activity in the patient's body). As shown in FIG. 16B, the bioelectrical signal $E_b$ is in series with the two half-cell potentials $E_1$, $E_2$, the sum of which may not be zero or stable. If the sum is not zero, the bioelectrical signal $E_b$ is superimposed on an offset or bias potential.

The impedance of the circuit between the electrode terminals includes two electrode-electrolyte impedances and that of tissue of the patient ($R_S$, $C_S$, $R_S'$). Because of physical characteristics of the patient's tissue and of the electrodes, the low-frequency impedance and will be high and the high-frequency impedance will be low, e.g., the high-frequency impedance will be similar to the impedance of just the patient's tissue. This is shown in the graph 1620 of FIG. 16C. The graph represents frequency response of the circuit model 1610. Thus, as frequency is increased, impedance decreases and the impedance asymptotically approaches $R_S'$. Accordingly, the impedance of elements of the circuit model 1610 (e.g., impedance of elements representing patient tissue) can be estimated by input of signals of multiple frequencies, e.g., signals of increasing frequency.

Figure 16D:
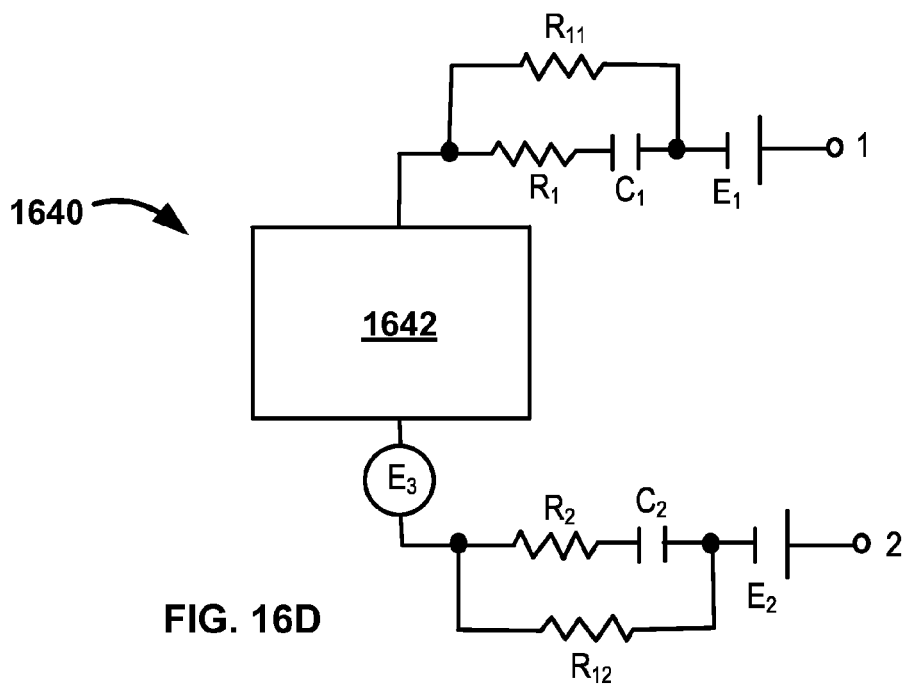

In some examples, the structure and components of the circuit model will vary depending on what patient tissue (e.g., what organ) is being modeled. Thus, while a particular circuit representing the patient ($R_S$, $C_S$, $R_S'$) is shown in FIG. 16B, other circuits may be used. FIG. 16D shows a circuit model 1640 that has a component 1642 representing the patient's tissue. In some examples, the component 1642 could be a circuit having a configuration of model electrical components (e.g., resistors, capacitors, etc.) that varies in the circuit model depending on the physical characteristics of the particular tissue.

Many other implementations other than those described may be employed, and may be encompassed by the following claims.

What is claimed is:

1. A computing device comprising:
a memory configured to store instructions; and
a processor to execute the instructions to perform operations comprising:
providing an alternating electrical signal to a patient through at least a pair of electrodes,
determining transthoracic impedance of the patient from a measurement associated with the applied alternating electrical signal, identifying, from the transthoracic impedance, a sequence of resistance values for controlling the discharge of a charge storage device located external to the patient, and controlling the discharge of the charge storage device using the identified sequence of resistance values by combining the transthoracic impedance with a respective resistance value of the sequence of resistance values to provide a substantially constant impedance level.

2. The computing device of claim 1, further comprising:
identifying, from the transthoracic impedance, a charge level for the charge storage device, and
charging the charge storage device based upon the identified charge level.

3. The computing device of claim 2, wherein determining the transthoracic impedance includes executing multiple impedance measurements.

4. The computing device of claim 3, wherein at least two of the multiple impedance measurements are used in determining a metric that represents consistency between the measurements.

5. The computing device of claim 4, wherein the operations further comprise:
identifying a predetermined value of impedance for the one or more operations of a defibrillator, upon determining that the metric fails to satisfy a threshold condition.

6. The computing device of claim 5, wherein the predetermined value is an impedance value associated with a previous defibrillation performed using the defibrillator.

7. The computing device of claim 1, wherein the operations further comprise:
using the transthoracic impedance in one or more operations of a defibrillator.

8. The computing device of claim 1, wherein the transthoracic impedance is calculated using at least two frequencies of the alternating electrical signal.

9. The computing device of claim 1, wherein a frequency of the alternating electrical signal is approximately 31 KHz.

10. The computing device of claim 1, wherein determining the transthoracic impedance of the patient includes measuring voltage across the patient.

11. The computing device of claim 1, wherein determining the transthoracic impedance includes executing impedance measurements for multiple frequencies.

12. The computing device of claim 11, wherein at least two defibrillation energies or current settings are used by the multiple frequency impedance measurements to estimate an expected impedance.

13. The computing device of claim 1, wherein the transthoracic impedance is one of a plurality of transthoracic impedances corresponding to a plurality of patients, such that the substantially constant impedance level is maintained for each of the plurality of patients over a cardiopulmonary resuscitation.

14. The computing device of claim 1, wherein the transthoracic impedance is one of a plurality of transthoracic impedances corresponding to a plurality of cardiopulmonary resuscitations, such that the substantially constant impedance level is maintained across the plurality of cardiopulmonary resuscitations.

15. The computing device of claim 14, wherein a first impedance level at a particular time relative to the start of a first cardiopulmonary resuscitation is substantially the same as a second impedance level at the particular time relative to the start of a second cardiopulmonary resuscitation.

16. The computing device of claim 1, wherein providing the substantially constant impedance level comprises applying a substantially constant current to the patient through the at least the pair of electrodes.

17. A medical device system comprising:
a defibrillator;
a memory configured to store instructions; and
a processor to execute the instructions to perform operations comprising:
providing an alternating electrical signal to a patient through at least a pair of electrodes,
determining transthoracic impedance of the patient from a measurement associated with the applied alternating electrical signal, wherein both real and complex values are calculated for the transthoracic impedance,
estimating a lumped circuit model of at least one electrode based on the real and complex values of the transthoracic impedance; and
providing an output representing a patient characteristic based on the lumped circuit model of the at least one electrode.

18. The medical device system of claim 17, wherein the operations further comprise:
using the determined transthoracic impedance in adjusting one or more operations of the defibrillator.

19. The medical device system of claim 17, wherein the transthoracic impedance is calculated using at least two frequencies of the alternating electrical signal.

20. The medical device system of claim 17, wherein a frequency of the alternating electrical signal is approximately 31 KHz.

21. The medical device system of claim 17, wherein determining transthoracic impedance of the patient includes measuring voltage across the patient.

22. The medical device system of claim 17, wherein determining transthoracic impedance includes executing impedance measurements for multiple frequencies.

23. The medical device system of claim 22, wherein at least two defibrillation energies or current settings are used by the multiple frequency impedance measurements to estimate an expected impedance.

24. The medical device system of claim 17, wherein the lumped circuit model includes estimates of elements of an electrode-electrolyte-skin (EES) interface.

25. The medical device system of claim 17, wherein the lumped circuit model includes estimates of values of lumped circuit elements of at least one organ of the patient.

26. The medical device system of claim 25, wherein the at least one organ is the heart.

27. The medical device system of claim 26, wherein changes in the estimate of values of lumped circuit elements of the heart are used to detect the flow of blood through the heart.

28. The medical device system of claim 25, wherein the at least one organ is the lungs.

29. The medical device system of claim 28, wherein changes in the estimate of values of lumped circuit elements are used to detect ventilations or spontaneous breathing.

30. The medical device system of claim 25, wherein the at least one organ is the brain.

31. The medical device system of claim 17, wherein the value of at least one element of the estimated lumped circuit model is used for artifact reduction in an electrically-based physiologic (EBP) signal.

32. The medical device system of claim 17, further comprising more than two electrodes.

33. The medical device system of claim 17, wherein determining transthoracic impedance includes executing multiple impedance measurements.

34. The medical device system of claim 33, wherein at least two of the multiple impedance measurements are used in determining a metric that represents consistency between the measurements.

35. The medical device system of claim 34, wherein the operations further comprise:
  identifying a predetermined value of impedance for the one or more operations of the defibrillator, upon determining that the metric fails to satisfy a threshold condition.

36. The medical device system of claim 35, wherein the predetermined value is an impedance value associated with a previous defibrillation performed using the defibrillator.

37. A non-transitory computer readable storage device storing instructions executable by a computing device to carry out operations comprising:

providing an alternating electrical signal to a patient through at least a pair of electrodes;

determining transthoracic impedance of the patient from a measurement associated with the applied alternating electrical signal;

identifying, from the transthoracic impedance, a sequence of resistance values for controlling the discharge of a charge storage device located external to the patient; and controlling the discharge of the charge storage device using the identified sequence of resistance values by combining the transthoracic impedance with a respective resistance value of the sequence of resistance values to provide a substantially constant impedance level.

* * * * *